United States Patent [19]
Winter et al.

[11] Patent Number: 5,204,473
[45] Date of Patent: Apr. 20, 1993

[54] O-SUBSTITUTED N-HYDROXY HINDERED AMINE STABILIZERS

[75] Inventors: Roland A. E. Winter, Armonk; James P. Galbo, Hartsdale; Raymond Seltzer, New City, all of N.Y.

[73] Assignee: Ciba-Geigy Corporation, Ardsley, N.Y.

[21] Appl. No.: 883,812

[22] Filed: May 12, 1992

Related U.S. Application Data

[63] Continuation of Ser. No. 749,470, Aug. 15, 1991, abandoned, which is a continuation of Ser. No. 614,569, Nov. 14, 1990, abandoned, which is a continuation of Ser. No. 259,950, Oct. 19, 1988, abandoned, which is a continuation-in-part of Ser. No. 99,414, Sep. 21, 1987, abandoned.

[51] Int. Cl.$^5$ .................. C07D 211/36; C07D 211/38; C07D 211/22
[52] U.S. Cl. .................. 546/188; 546/189; 546/225; 546/242; 544/194; 544/207; 544/231; 544/357; 544/360
[58] Field of Search .................. 546/19, 20, 187–189, 546/225, 242; 544/194, 207, 231, 357, 360

[56] References Cited

U.S. PATENT DOCUMENTS

| | | | |
|---|---|---|---|
| 4,344,876 | 8/1982 | Berrer | 524/91 |
| 4,547,537 | 0/1985 | Malherbe et al. | 524/97 |
| 4,691,015 | 9/1987 | Behrens | 546/19 |
| 4,774,275 | 0/1988 | Hisano et al. | 524/370 |

OTHER PUBLICATIONS

J. Polymer Science, Chem. Ed., 22, 277–81 (1984).
Chem. Abstracts 100, 52579y (1983).
Japan 86-130,358 (1986)–abstract.
Shlyapintokh, Developments in Polymer Stabilization 1982, pp. 41–70.

*Primary Examiner*—John W. Rollins
*Attorney, Agent, or Firm*—Luther A. R. Hall

[57] ABSTRACT

Hindered amines based on various 2,2,6,6-tetraalkylated nitrogen-containing heterocyclic moieties wherein the hindered nitrogen atom on the ring is substituted with $OR_1$ substituents and the 4-position of the ring is substituted with a variety of groups, are effective as light stabilizers in diverse substrate systems.

36 Claims, No Drawings

O-SUBSTITUTED N-HYDROXY HINDERED AMINE STABILIZERS

RELATED APPLICATION

This is a continuation of application Ser. No. 749,470, filed on Aug. 15, 1991, now abandoned, which is a continuation of application Ser. No. 614,569, filed on Nov. 14, 1990, now abandoned, which is a continuation of application Ser. No. 259,950, filed on Oct. 19, 1988, now abandoned, which is a continuation-in-part of application Ser. No. 099,414, filed on Sep. 21, 1987, now abandoned.

BACKGROUND OF THE INVENTION

The invention relates to novel hindered amine derivatives containing $OR_1$ groups on the hindered nitrogen atom of the nitrogen-containing heterocyclic ring and a diversity of substituents on the 4-position of the ring.

Various N-alkoxy hindered amine derivatives containing a single piperidine ring are known. For example, O-alkyl derivatives with hydrogen in the 4-position are disclosed in Kurumada et al, *J. Polym. Sci, Polym. Chem. Ed.* 23, 1477-91 (1985); Bolsman et al, *Rec. Trav. Chim. Pays-Bas* 97, 313-19 (1978); and Sholle et al, *Dokl. Akad. Nauk SSSR*, Chem. Sect. 200, 137-9 (1971). Similar derivatives with benzoyloxy in the 4-position are noted in Kurumada et al, *J. Polym. Sci.,* Polym. Chem. Ed. 22, 277-81 (1984). Cyano-substituted alkoxy substituents are disclosed in Australian 30378/84 while amido-substituted alkoxy substituents are disclosed in Japanese 74/40557. U.S. Pat. No. 4,547,537 disclose N-alkoxy piperidyl compounds with tetrahydro-1,4-oxazine-2-one group linked to the piperidine ring. N-aralkoxy substituents on hindered piperidine rings are also disclosed in Keana et al, *J. Org. Chem.* 36, 209-11 (1971) and Howard et al, *J. Org. Chem.* 43, 4279-83 (1978). N-alpha-hydroxy-alkoxy substituents on piperidinones are noted in Wilson, *Trans. Far. Soc.* 67, 3508-19 (1971). Mead et al, *Aust. J. Chem.* 36, 1573-88 (1983) disclose various O-substituents having unsaturation and/or carboxyl groups in the chain. Finally, Fujita et al, *J. Polym. Sci.,* Polym. Lett Ed. 16, 515-18 (1978) disclose di-piperidinoxy dioxospiro compounds which are able to prevent degradation of several synthetic polymers.

Accordingly, it is the object of this invention to identify a series of new $OR_1$-substituted N-hydroxy hindered amines having a broad range of stabilization performance characteristics.

The instant invention thus relates to hydroxylamine derivatives having one of formulae A to O

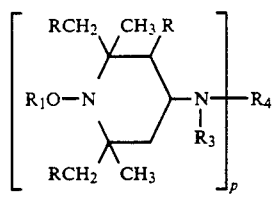
(A)

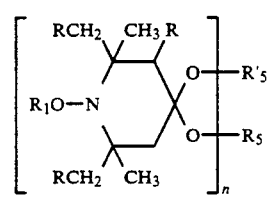
(B)

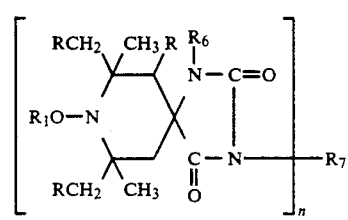
(C)

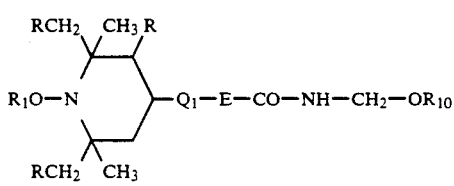
(D)

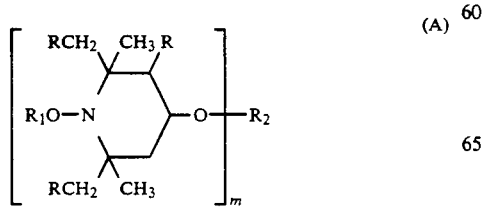
(E)

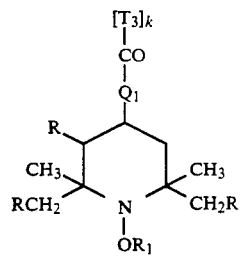
(F)

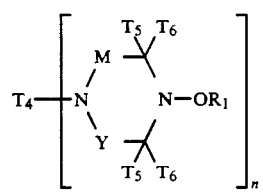
(G)

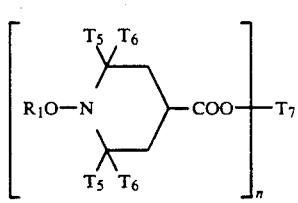
(H)

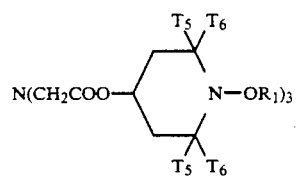
(I)

-continued

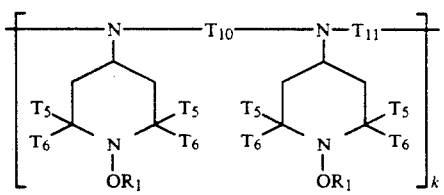
(J)

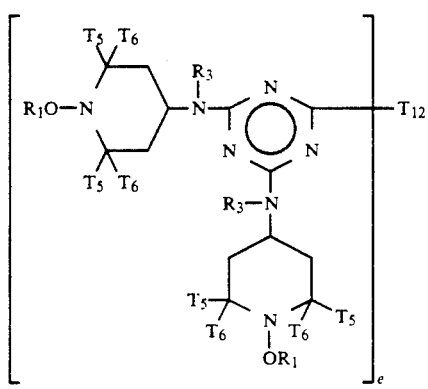
(K)

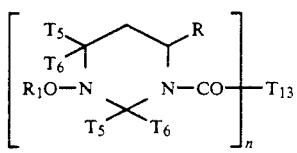
(L)

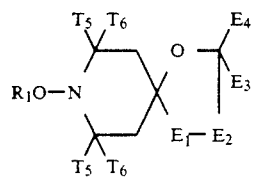
(M)

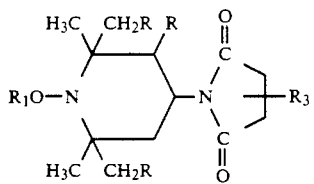
(N)

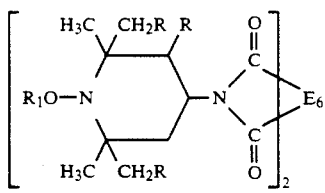
(O)

wherein
R is hydrogen or methyl,
$R_1$ is independently $C_1$-$C_{18}$ alkyl, $C_2$-$C_{18}$ alkenyl, $C_2$-$C_{18}$ alkynyl, $C_5$-$C_8$ cycloalkenyl, $C_5$-$C_{12}$ cycloalkyl, $C_6$-$C_{10}$ bicycloalkyl, $C_6$-$C_{10}$ aryl, $C_7$-$C_9$ aralkyl, or $C_7$-$C_9$ aralkyl substituted by alkyl or aryl;
m is 2–4;
when m is 2,
$R_2$ is $C_1$-$C_{12}$ alkylene, $C_4$-$C_{12}$ alkenylene, xylylene, a divalent acyl radical of an aliphatic, cycloaliphatic, araliphatic or aromatic dicarboxylic acid, or of a dicarbamic acid, preferably an acyl radical of an aliphatic dicarboxylic acid having 2–18 C atoms, of a cycloaliphatic or aromatic dicarboxylic acid having 8–14 C atoms or of an aliphatic, cycloaliphatic or aromatic dicarbamic acid having 8–14 C atoms;

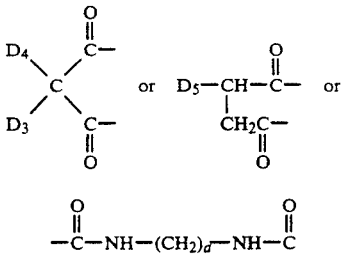

wherein $D_3$ and $D_4$ are independently hydrogen, an alkyl radical containing up to 8 carbon atoms, an aryl or aralkyl radical including 3,5-di-t-butyl-4-hydroxybenzyl radical, $D_5$ is hydrogen, or an alkyl or alkenyl radical containing up to 18 carbon atoms, and d is 0–20;
when m is 3, $R_2$ is a trivalent acyl radical of an aliphatic, unsaturated aliphatic, cycloaliphatic, or aromatic tricarboxylic acid;
when m is 4, $R_2$ is a tetravalent acyl radical of a saturated or unsaturated aliphatic or aromatic tetracarboxylic acid including 1,2,3,4-butanetetracarboxylic acid, 1,2,3,4-but-2-enetetracarboxylic acid, and 1,2,3,5- and 1,2,4,5-pentanetetracarboxylic acid;
p is 1, 2 or 3;
$R_3$ is hydrogen, $C_1$-$C_{12}$ alkyl, $C_5$-$C_7$ cycloalkyl, $C_7$-$C_8$ aralkyl, $C_2$-$C_{18}$ alkanoyl, $C_3$-$C_5$ alkenoyl or benzoyl;
when p is 1,
$R_4$ is hydrogen, $C_1$-$C_{18}$ alkyl, $C_5$-$C_7$ cycloalkyl, $C_2$-$C_8$ alkenyl unsubstituted or substituted by a cyano, carbonyl or carbamide group, aryl, aralkyl, glycidyl, a group of the formula —$CH_2$—CH(OH)—Z or of the formula —CO—Z or —CONH—Z wherein Z is hydrogen, methyl or phenyl; or a group of the formula

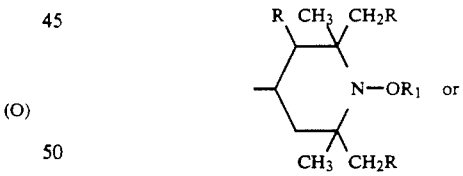

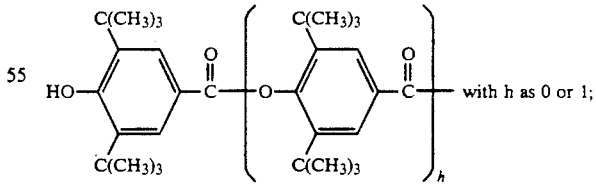 with h as 0 or 1;

or $R_3$ and $R_4$ together can be alkylene of 4 to 6 carbon atoms or 2-oxo-polyalkylene or the cyclic radical of an aliphatic or aromatic 1,2- or 1,3-dicarboxylic acid,
when p is 2,
$R_4$ is a direct bond or is $C_1$-$C_{12}$ alkylene, $C_6$-$C_{12}$ arylene, xylylene, a —$CH_2$CH(OH)—$CH_2$ group, or a group —$CH_2$—CH(OH)—$CH_2$—O—X—O—$CH_2$—CH(OH)—$CH_2$— wherein X is $C_2$-$C_{10}$ alkylene, $C_6$-$C_{15}$ arylene or $C_6$-$C_{12}$ cycloalkylene; or, provided that $R_3$ is not alkanoyl, alkenoyl or benzoyl, $R_4$ can also be a divalent acyl radical of an aliphatic, cycloaliphatic or aromatic dicarboxylic acid or of a dicarbamic acid, or can be the group —CO—; or $R_4$ is

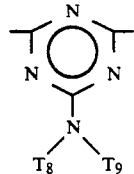

where $T_8$ and $T_9$ are independently hydrogen, alkyl of 1 to 18 carbon atoms, or $T_8$ and $T_9$ together are alkylene of 4 to 6 carbon atoms or 3-oxapentamethylene, preferably $T_8$ and $T_9$ together are 3-oxapentamethylene;

when p is 3, $R_4$ is 2,4,6-triazinyl, n is 1 or 2, when n is 1, $R_5$ and $R'_5$ are independently $C_1$-$C_{12}$ alkyl, $C_2$-$C_{12}$ alkenyl, $C_7$-$C_{12}$ aralkyl, or $R_5$ is also hydrogen, or $R_5$ and $R'_5$ together are $C_2$-$C_8$ alkylene or hydroxyalkylene or $C_4$14 $C_{22}$ acyloxyalkylene;

when n is 2, $R_5$ and $R'_5$ together are $(—CH_2)_2C(CH_2—)_2$;

$R_6$ is hydrogen, $C_1$-$C_{12}$ alkyl, allyl, benzyl, glycidyl or $C_2$-$C_6$ alkoxyalkyl;

when n is 1, $R_7$ is hydrogen, $C_1$-$C_{12}$ alkyl, $C_3$-$C_5$ alkenyl, $C_7$-$C_9$ aralkyl, $C_5$-$C_7$ cycloalkyl, $C_2$-$C_4$ hydroxyalkyl, $C_2$-$C_6$ alkoxyalkyl, $C_6$-$C_{10}$ aryl, glycidyl, a group of the formula —$(CH_2)_t$—COO—Q or of the formula —$(CH_2)_t$—O—CO—Q wherein t is 1 or 2, and Q is $C_1$-$C_4$ alkyl or phenyl; or when n is 2, $R_7$ is $C_2$-$C_{12}$ alkylene, $C_6$-$C_{12}$ arylene, a group —$CH_2CH(OH)$—$CH_2$—O—X—O—$CH_2$—$CH(OH)$—$CH_2$— wherein X is $C_2$-$C_{10}$ alkylene, $C_6$-$C_{15}$ arylene or $C_6$-$C_{12}$ cycloalkylene, or a group —$CH_2CH(OZ')CH_2$—$(OCH_2$—$CH(OZ')CH_2)_2$— wherein Z' is hydrogen, $C_1$-$C_{18}$ alkyl, allyl, benzyl, $C_2$-$C_{12}$ alkanoyl or benzoyl;

$Q_1$ is —$N(R_8)$— or —O—; E is $C_1$-$C_3$ alkylene, the group —$CH_2$—$CH(R_9)$—O— wherein $R_9$ is hydrogen, methyl or phenyl, the group —$(CH_2)_3$—NH— or a direct bond;

$R_{10}$ is hydrogen or $C_1$-$C_{18}$ alkyl, $R_8$ is hydrogen, $C_1$-$C_{18}$ alkyl, $C_5$-$C_7$ cycloalkyl, $C_7$-$C_{12}$ aralkyl, cyanoethyl, $C_6$-$C_{10}$ aryl, the group —$CH_2$—$CH(R_9)$—OH wherein $R_9$ has the meaning defined above; a group of the formula

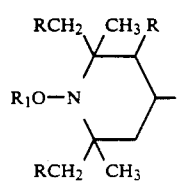

or a group of the formula

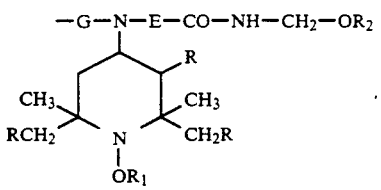

wherein G is $C_2$-$C_6$ alkylene or $C_6$-$C_{12}$ arylene; or $R_8$ is a group —E—CO—NH—$CH_2$—$OR_{10}$;

Formula F denotes a recurring structural unit of a polymer where $T_3$ is ethylene or 1,2-propylene, or is the repeating structural unit derived from an alpha-olefin copolymer with an alkyl acrylate or methacrylate; preferably a copolymer of ethylene and ethyl acrylate, and where k is 2 to 100;

$T_4$ has the same meaning as $R_4$ when p is 1 or 2, $T_5$ is methyl, $T_6$ is methyl or ethyl, or $T_5$ and $T_6$ together are tetramethylene or pentamethylene, preferably $T_5$ and $T_6$ are each methyl, M and Y are independently methylene or carbonyl preferably M is methylene and Y is carbonyl, and $T_4$ is ethylene where n is 2;

$T_7$ is the same as $R_7$, and $T_7$ is preferably octamethylene where n is 2, $T_{10}$ and $T_{11}$ are independently alkylene of 2 to 12 carbon atoms, or $T_{11}$ is

$T_{12}$ is piperazinyl, —$NR_{11}$—$(CH_2)_d$—$NR_{11}$— or

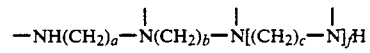

where $R_{11}$ is the same as $R_3$ and is also

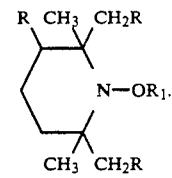

a, b and c are independently 2 or 3, and f is 0 or 1, preferably d is 1-8, a and c are each 3, b is 2 and f is 1; and e is 2, 3 or 4, preferably 4;

$T_{13}$ is the same as $R_2$ with the proviso that $T_{13}$ cannot be hydrogen when n is 1;

$E_1$ and $E_2$, being different, each are —CO— or —N($E_5$)— where $E_5$ is hydrogen, $C_1$-$C_{12}$ alkyl or $C_4$-$C_{22}$ alkoxycarbonylalkyl, preferably $E_1$ is —CO— and $E_2$ is —$N(E_5)$—, $E_3$ is hydrogen, alkyl of 1 to 30 carbon atoms, phenyl, naphthyl, said phenyl or said naphthyl substituted by chlorine or by alkyl of 1 to 4 carbon atoms, or phenylalkyl of 7 to 12 carbon atoms, or said phenylalkyl substituted by alkyl of 1 to 4 carbon atoms, $E_4$ is hydrogen, alkyl of 1 to 30 carbon atoms, phenyl, naphthyl or phenylalkyl of 7 to 12 carbon atoms, or $E_3$ and $E_4$ together are polymethylene of 4 to 17 carbon atoms, or said polymethylene substituted by up to four alkyl groups of 1 to 4 carbon atoms, preferably methyl, and $E_6$ is an aliphatic or aromatic tetravalent radical.

In the structures A to O, if any substituents are $C_1$–$C_{18}$ alkyl, they are for example methyl, ethyl, n-propyl, n-butyl, sec-butyl, tert-butyl, n-hexyl, n-octyl, 2-ethylhexyl, n-nonyl, n-decyl, n-undecyl, n-dodecyl, n-tridecyl, n-tetradecyl, n-hexadecyl or n-octadecyl. Typical cycloalkyl groups include cyclopentyl, cyclohexyl and cyclododecyl; typical cycloalkenyl groups include cyclohexenyl; while typical aralkyl groups include benzyl, alpha-methylbenzyl, alpha,alpha-dimethylbenzyl or phenethyl. $C_1$–$C_{12}$ alkyl and cyclohexyl are preferred.

If $R_2$ is a divalent acyl radical of a dicarboxylic acid, it is for example an acyl radical of oxalic acid, adipic acid, succinic acid, suberic acid, sebacic acid, phthalic acid, isophthalic acid, terephthalic acid, dibutylmalonic acid, dibenzylmalonic acid, (3,5-di-tert-butyl-4-hydroxybenzyl)-malonic acid, or bicycloheptenedicarboxylic acid, with succinates, sebacates, phthalates and isophthalates being preferred.

If $R_2$ is a divalent acyl radical of a dicarbamic acid, it is for example an acyl radical of hexamethylenedicarbamic acid or of 2,4-toluylenedicarbamic acid.

The following compounds are examples of polyalkylpiperidine starting materials useful in making the hydroxylamine derivatives of formula A. (Relates to the selected preparative procedure).

di-(2,2,6,6-tetramethylpiperidin-4-yl) adipate
di-(2,2,6,6-tetramethylpiperidin-4-yl) sebacate
di-(2,2,6,6-tetramethylpiperidin-4-yl) phthalate
alpha,alpha'-(di-2,2,6,6-tetramethylpiperidine-4-oxy)-p-xylene
di-(2,2,6,6-tetramethylpiperidin-4-yl) succinate
di-(2,2,6,6-tetramethylpiperidin-4-yl) malonate
di-(1-oxyl-2,2,6,6-tetramethylpiperidin-4-yl) isophthalate
4-hydroxy-1-methoxy-2,2,6,6-tetramethylpiperidine
di-(1-hydroxy-2,2,6,6-tetramethylpiperidin-4-yloxy)-p-xylene
1-ethoxy-4-hydroxy-2,2,6,6-tetramethylpiperidine
(2,2,6,6-tetramethylpiperidin-4-yl)-[4-(2-oxoazepin-1-yl)-2,2,6,6-tetramethylpiperidin-4-yl]acetate.

As $C_2$–$C_{18}$ alkanoyl, $R_3$ is for example propionyl, butyryl, octanoyl, dodecanoyl, hexadecanoyl, octadecanoyl, but preferably acetyl.

If $R_4$ is $C_2$–$C_8$ alkenyl unsubstituted or substituted by a cyano, carbonyl or carbamide group, it is for example 1-propenyl, allyl, methallyl, 2-butenyl, 2-pentenyl, 2-hexenyl, 2-octenyl, 2,2-dicyanovinyl, 1-methyl-2-cyano-2-methoxycarbonyl-vinyl or 2,2-diacetylaminovinyl.

If any substituents are $C_2$–$C_{12}$ alkylene, they are for example ethylene, propylene, 2,2-dimethylpropylene, tetramethylene, hexamethylene, octamethylene, decamethylene or dodecamethylene.

If any substituents are $C_6$–$C_{15}$ arylene, they are for example o-, m- or p-phenylene, 1,4-naphthylene or 4,4'-diphenylene.

As $C_6$–$C_{12}$ cycloalkylene, X is especially cyclohexylene.

The following compounds are examples of polyalkylpiperidine starting materials useful in making the hydroxylamine derivatives of formula B.

N,N'-bis(2,2,6,6-tetramethylpiperidin-4-yl)-hexamethylene-1,6-diamine,
N,N'-bis-(2,2,6,6-tetramethylpiperidin-4-yl)-hexamethylene-1,6-diacetamide,
4-benzylamino-2,2,6,6-tetramethylpiperidine,
N-n-butyl-N-(2,2,6,6-tetramethylpiperidin-4-yl)-4-hydroxy-3,5-di-tert.butylbenzamide,
N,N'-bis-(2,2,6,6-tetramethylpiperidin-4-yl)-N,N'-dibutyl-adipamide,
N,N'-bis-(2,2,6,6-tetramethylpiperidin-4-yl)-N,N'-dicyclohexyl-(2-hydroxypropylene-diamine),
N,N'-bis-(2,2,6,6-tetramethylpiperidin-4-yl)-p-xylylenediamine,
4-(3-methyl-4-hydroxy-5-tert-butyl-benzoyl acetamido)-2,2,6,6-tetramethylpiperidine,
alpha-cyano-$\beta$-methyl-$\beta$-[N-(2,2,6,6-tetramethylpiperidin-4-yl]-amino-acrylic acid methyl ester.
1-oxyl-2,2,6,6-tetramethylpiperdino-4-one If $R_5$ is $C_2$–$C_8$ alkylene or hydroxyalkylene, it is for example ethylene, 1-methyl-ethylene, propylene, 2-ethylpropylene or 2-ethyl-2-hydroxymethylpropylene.

As $C_4$–$C_{22}$ acyloxyalkylene, $R_5$ is for example 2-ethyl-2-acetoxymethyl-propylene.

The following compounds are examples of polyalkylpiperidine starting materials useful in making the hydroxylamine derivatives of formula C.

9-aza-8,8,10,10-tetramethyl-1,5-dioxaspiro[5.5]undecane,
9-aza-8,8,10,10-tetramethyl-3-ethyl-1,5-dioxaspiroundecane,
2,2,6,6-tetramethylpiperidine-4-spiro-2'-(1',3'-dioxane)-5'-spiro-5''-(1'',3''-dioxane)-2''-spiro-4'''-(2''',2'''-6''',6'''-tetramethylpiperidine).

If any substituents are $C_2$–$C_6$ alkoxyalkyl, they are for example methoxymethyl, ethoxymethyl, propoxymethyl, tert-butoxyethyl, ethoxyethyl, ethoxypropyl, n-butoxyethyl, tert-butoxyethyl, isopropoxyethyl or propoxypropyl.

If $R_7$ is $C_3$–$C_5$ alkenyl, it is for example 1-propenyl, allyl, methallyl, 2-butenyl or 2-pentenyl.

As $C_7$–$C_9$ aralkyl, $R_7$ is in particular phenethyl or above all benzyl; and as $C_5$–$C_7$ cycloalkyl, $R_7$ is especially cyclohexyl.

If $R_7$ is $C_2$–$C_4$ hydroxyalkyl, it is for example 2-hydroxyethyl, 2-hydroxypropyl, 3-hydroxypropyl, 2-hydroxybutyl or 4-hydroxybutyl.

As $C_6$–$C_{10}$ aryl, $R_1$ and $R_7$ are in particular phenyl, or alpha- or $\beta$-naphthyl which is unsubstituted or substituted by halogen or $C_1$–$C_4$ alkyl.

If $R_7$ is $C_2$–$C_{12}$ alkylene, it is for example ethylene, propylene 2,2-dimethylpropylene, tetramethylene, hexamethylene, octamethylene, decamethylene or dodecamethylene.

If $R_7$ is $C_6$–$C_{12}$ arylene, it is for example o-, m- or p-phenylene, 1,4-naphthylene or 4,4'-diphenylene.

If Z' is $C_2$–$C_{12}$ alkanoyl, it is for example propionyl, butyryl, octanoyl, dodecanoyl or preferably acetyl.

The following compounds are examples of polyalkylpiperidine starting materials useful in making hydroxylamine derivatives of formula D.

3-benzyl-1,3,8-triaza-7,7,9,9-tetramethylspiro[4.5]decane-2,4-dione,
3-n-octyl-1,3,8-triaza-7,7,9,9-tetramethylspiro[4.5]decane-2,4-dione, 3-allyl-1,3,8-triaza-1,7,7,9,9-pentamethylspiro[4.5]dec-
ane-2,4-dione,
or the compounds of the following formulae:

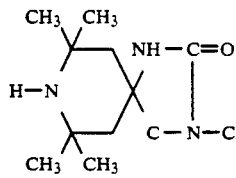 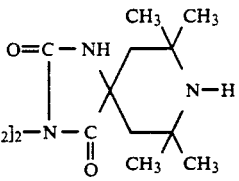

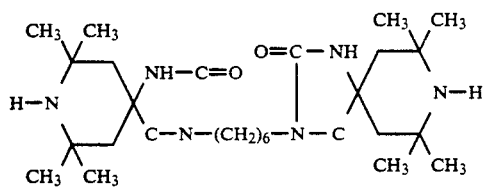

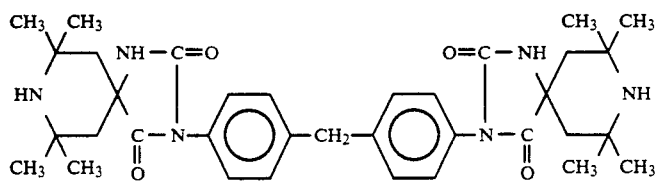

As $C_5$–$C_7$ cycloalkyl, $R_8$ in particular cyclohexyl.

As $C_6$–$C_{10}$ aryl, $R_8$ is particularly phenyl, or alpha- or β-naphthyl which is unsubstituted or substituted with halogen or $C_1$–$C_4$ alkyl. As $C_1$–$C_3$ alkylene, E is for example methylene, ethylene or propylene.

As $C_2$–$C_6$ alkylene, G is for example ethylene, propylene, 2,2-dimethylpropylene, tetramethylene or hexamethylene; and as $C_6$–$C_{12}$ arylene, G is o-, m- or p-phenylene, 1,4-naphthylene or 4,4'-diphenylene.

The following compounds are examples of polyalkylpiperidine starting materials useful in making the hydroxylamine derivatives of formula E.

N-hydroxymethyl-N'-2,2,6,6-tetramethylpiperidin-4-yl-urea,

N-methoxymethyl-N'-2,2,6,6-tetramethylpiperidin-4-ylurea,

N-methoxymethyl-N'-n-dodecyl-N'-2,2,6,6-tetramethylpiperidin-4-yl-urea, and

O-(2,2,6,6-tetramethylpiperidin-4-yl)-N-methoxymethylurethane.

When the instant hydroxylamine derivative is of formula F, the following polymeric compounds are examples of starting materials useful in preparing said derivatives.

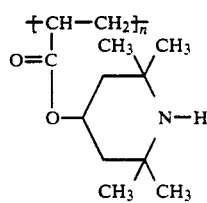

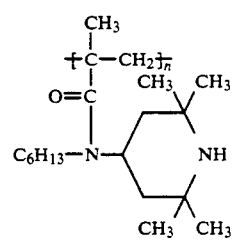

Additional starting hindered amine derivatives include for formula J:
poly-{[6-[(1,1,3,3-tetramethylbutyl)-imino]-1,3,5-triazine-2,4-diyl][2-(1-oxyl-2,2,6,6-tetramethylpiperidyl)-imino]-hexamethylene-4-[4-(1-oxyl-2,2,6,6-tetramethylpiperidyl]-imino]}.

For compounds of formula N, $R_3$ is preferably $C_1$–$C_{12}$ alkyl and $C_5$–$C_7$ cycloalkyl and more preferably methyl, octyl, dodecyl and cyclohexyl.

For compounds of formula O, the following species are typical of tetracarboxylic acid dianhydrides suitable for the preparation thereof:
2,3,9,10-perylene tetracarboxylic acid dianhydride
1,4,5,8-naphthalene tetracarboxylic acid dianhydride
2,6-dichloronaphthalene-1,4,5,8-tetracarboxylic acid dianhydride
2,7-dichloronaphthalene-1,4,5,8-tetracarboxylic acid dianhydride
2,3,6,7-tetrachloronaphthalene-1,4,5,8-tetracarboxylic acid dianhydride
phenanthrene-1,8,9,10-tetracarboxylic acid dianhydride
2,3,3',4'-benzophenonetetracarboxylic acid dianhydride
pyromellitic dianhydride
3,3',4,4'-benzophenonetetracarboxylic acid dianhydride
2,2',3,3'-benzophenonetetracarboxylic acid dianhydride
3,3',4,4'-biphenyltetracarboxylic acid dianhydride
2,2',3,3'-biphenyltetracarboxylic acid dianhydride
4,4'-isopropylidenediphthalic anhydride
3,3'-isopropylidenediphthalic anhydride
4,4'-oxydiphthalic anhydride
4,4'-sulfonyldiphthalic anhydride
3,3'-oxydiphthalic anhydride 4,4'-methylenediphthalic anhydride
4,4'-thiodiphthalic anhydride
4,4'-ethylidenediphthalic anhydride
2,3,6,7-naphthalenetetracarboxylic acid dianhydride
1,2,4,5-naphthalenetetracarboxylic acid dianhydride
1,2,5,6-naphthalenetetracarboxylic acid dianhydride
benzene-1,2,3,4-tetracarboxylic acid dianhydride
pyrazine-2,3,5,6-tetracarboxylic acid dianhydride.

The hydroxylamine derivatives of the instant invention are generally prepared by oxidizing the corresponding hindered amine with an appropriate peroxy compound such as hydrogen peroxide or tert-butyl hydroperoxide in the presence of a metal carbonyl or metal oxide catalyst followed by reduction of the oxyl intermediate formed to the desired N-hydroxy derivative, preferably by catalytic hydrogenation.

Thereafter, the O-alkyl substituted N-hydroxy derivatives can be synthesized by several routes. For example, the N-hydroxy derivative can be alkylated with sodium hydride and halogenated hydrocarbons such as benzyl bromide and ethyl iodide. N-methoxy variants can be prepared by thermolysis of a chlorobenzene solution of nitroxyl radical and di-tert-butyl peroxide The product is formed by a coupling reaction betwen the nitroxyl radical and the methyl radical generated from β-scission of a t-butoxy radical.

Other N-alkoxy variants can be synthesized by coupling nitroxyl radicals with hydrocarbon radicals generated from thermal decomposition of di-tert-butyl peroxide in the presence of hydrocarbon solvents such as cyclohexane, toluene, and ethylbenzene.

A preferred approach is the preparation of N-alkoxy hindered amines directly from hindered amines. For example, a mixture of 4-benzoyloxy-2,2,6,6-tetramethylpiperidine, aqueous t-butyl hydroperoxide, molybdenum oxide, and ethylbenzene gives a 90% yield of N-alpha-methylbenzyloxy HALS. Molybdenum (VI) has been shown to increase the efficiency of both the oxidation of hindered amine to nitroxyl radical and the reaction of nitroxyl radicals with hydrocarbons.

Although these procedures have been referenced in terms of N-alkoxy substituents, they are meant to equally apply to all $OR_1$ groups.

The hindered amine precursors are largely commercially available or can be prepared by the application of known methods.

Reference is made to Kurumada et al, *J. Polym. Sci.,* Poly. Chem. Ed. 23, 1477-91 (1985), Mead et al, *Aust. J. Chem.* 36, 1573-88 (1983) and U.S. Pat. No. 4,547,537 in this regard.

The derivatives are particularly effective in stabilizing organic materials against the degradative effects of actinic stimuli. Such organic materials include polyolefins, elastomers, polyvinyl chloride, polyesters and polyurethanes. They also exhibit improved antioxidant activity in polyolefins relative to corresponding NH derivatives. Thus, the substrates are protected during processing and the gas fading that may be experienced upon exposure to the combination products of natural gas is signficantly reduced. They are particularly active as light stabilizers in ambient cured and acid catalyzed thermoset coatings or enamels. Since these materials are considerably less basic than conventional hindered amines, they do not inhibit or interfere with cure as is encountered with the conventional hindered amines. They likewise do not exhibit the color problems encountered with nitroxyl radicals and, in contrast to N-hydroxy derivatives, tend to resist air oxidation during handling. Finally, the N-alkoxy hindered amines exhibit greater solubility in the solvents typically utilized in coatings. These areas are further described in U.S. application Ser. Nos. 99,411 and 99,420.

The following examples will further illustrate the embodiments of this invention.

EXAMPLE 1

Di-(1-methoxy-2,2,6,6-tetramethylpiperidin-4-yl) Isophthalate

A solution of 30.0 g (73 mmol) of di-(1-oxyl-2,2;6,6-tetramethylpiperidin-4-yl) isophthalate and 27.8 g (190 mmol) of di-tert-butyl peroxide in 70 ml of chlorobenzene is heated for 6 hours in a nitrogen atmosphere in a Fisher-Porter bottle (bath temp. 145°-50° C.). The crude reaction mixture is chromatographed on silica gel (98:2 heptane: ethyl acetate) to obtain solid, which is recrystallized from methanol to afford the title compound, a white crystalline solid, m.p. 99°-101° C.

Anal. Calcd. for $C_{28}H_{44}N_2O_6$: C, 66.6; H, 8.8; N, 5.55. Found: C, 66.4; H, 8.7; N, 5.5.

EXAMPLE 2

Di-(1-methoxy-2,2,6,6-tetramethylpiperidin-4-yl) Sebacate

4-Benzoyloxy-1-methoxy-2,2,6,6-tetramethylpiperidine (8.0 g, 32 mmol) is stirred for 2 hr. at 60°-70° C. (nitrogen atmosphere) with 2.2 g (39 mmol) of potassium hydroxide in 300 ml of 1:1 (v/v) methanol:water. Solvent is removed under reduced pressure to obtain a white solid, which is partitioned between water (100 ml) and dichloromethane (150 ml). The aqueous layer is washed with dichloromethane (2×150 ml). The organic layers are combined and washed with water (100 ml) and saturated sodium chloride (100 ml), then dried over magnesium sulfate and concentrated to afford 5.7 g of crude 4-hydroxy-1-methyl-2,2,6-tetramethylpiperidine, methylpiperidine, a white solid with mp 92.5°-93.5° C. IR: 3250 cm$^{-1}$.

A solution of 5.4 g (29 mmol) of 4-hydroxy-1-methoxy-2,2,6,6-tetramethylpiperidine, 3.2 g (13.9 mmol) of dimethyl sebacate, and 200 ml of toluene is distilled for 45 minutes to azeotrope any water present. The solution is allowed to cool and 150 mg of lithium amide is added. The reaction mixture is slowly distilled for 5 hr. to remove methanol along with some of the toluene. The remaining toluene is then removed at reduced pressure. The reaction mixture is cooled to 5° C. and water (20 ml) is added. The organic material is dissolved in ethyl acetate (200 ml). The aqueous layer is extracted with ethyl acetate (2×100 ml). The combined organic layers are washed with water (2×50 ml) and saturated sodium chloride (50 ml), then dried over magnesium sulfate and concentrated under reduced pressure. The crude liquid is chromatographed on silica gel (95:5 heptane: ethyl acetate) to obtain 5.4 g (68% overall yield) of the title compound, a colorless liquid. IR: 1750 cm$^{-1}$.

Anal. Calcd. for $C_{30}H_{56}N_2O_6$: C, 66.6, H, 10.4; N, 5.2. Found: C, 66.7, H, 10.4; N, 5.0.

EXAMPLE 3 alpha,alpha'-(Di-1-ethoxy-2,2,6,6-tetramethylpiperidin-4-yloxy)-p-xylene

A mixture of 9.0 g (20.1 mmol) of alpha,alpha'-(di-1-hydroxy-2,2,6,6-tetramethylpiperidin-4-yloxy)-p- xylene, 1.8 g (44.2 mmol) of sodium hydride, and 100 ml of tetrahydrofuran (THF) is refluxed under nitrogen for 2 hr. The reaction mixture is cooled to 50° C. and excess ethyl iodide (7.5 g, 48.2 mmol) is added. The reaction mixture is refluxed for 2 hr. Additional sodium hydride (1.8 g), ethyl iodide (7.5 g) and 1.0 ml of t-butyl alcohol are then added, and the reaction mixture is refluxed for 16 hr. The reaction mixture is cooled and methanol is added. The reaction mixture is partitioned between water (600 ml) and diethyl ether (200 ml). The aqueous layer is extracted with ether (200 ml). The combined organic layers are washed with water (200 ml) and saturated sodium chloride (200 ml), then dried over magnesium sulfate and concentrated to obtain a yellow oil. The oil is chromatographed on silica gel (4:1 hexane:ethyl acetate) to obtain a crude solid which is successively recrystallized from cold methanol and hexane. The yield is 7.9 g (78%) of a white solid, mp 99°–101° C.

Anal. Calcd. for $C_{30}H_{52}N_2O_4$: C, 71.4; H, 10.4; N, 5.5. Found: C, 71.6; H, 10.8; N, 5.5.

EXAMPLE 4

Di-(1-cyclohexyloxy-2,2,6,6-tetramethylpiperidin-4-yl) Sebacate

A mixture of 20.0 g (41.6 mmol) of di-(2,2,6,6-tetramethylpiperidin-4-yl) sebacate, 43 g (334 mmol) of 70% aqueous t-butyl hydroperoxide, 1.3 g (9.0 mmol) of molybdenum trioxide, and 125 ml of cyclohexane is heated at reflux for 2.3 hours. Water is collected in a Dean-Stark trap. The red reaction mixture is cooled and transferred to a Fischer-Porter bottle. Fresh cyclohexane (25 ml) is used to thoroughly rinse the flask, and the rinsings are added to the pressure bottle. The pressure bottle is immersed in an oil bath (140° C.) for 3 hours whereupon the colorless reaction mixture is cooled to room temperature and filtered. The filtrate is stirred with 10 g of sodium sulfite in 90 ml of water for 2 hours to decompose unreacted hydroperoxide, then diluted with ethyl acetate (200 ml) and water (100 ml). The organic layer is washed with 10% sodium sulfite (100 ml), water (100 ml), saturated sodium chloride (100 ml), then dried over magnesium sulfate and concentrated at reduced pressure. The crude product is purified by flash chromatography (silica gel, 100:2 heptane:ethyl acetate) to afford 17.8 g (63% yield) of a white solid, m.p. 56°–9° C.

Anal. Calcd. for $C_{40}H_{72}N_2O_6$: C, 71.0; H, 10.7; N, 4.1. Found: C, 71.0; H, 10.2; N, 4.2.

EXAMPLE 5

Di-(1-cyclohexyloxy-2,2,6,6-tetramethylpiperidin-4-yl) Isophthalate

A solution of 34.2 g of di-(1-oxyl-2,2,6,6-tetramethylpiperidin-4-yl) isophthalate and 54 ml of di-tert-butyl peroxide in 250 ml of cyclohexane is heated for 22 hours in a nitrogen atmosphere in a Fisher-Porter bottle (bath temperature of 140° C.). Solvent is evaporated under reduced pressure. The product is recrystallized from pentane to give a white solid, mp 140°–42° C.

Anal. Calcd. for $C_{38}H_{56}N_2O_6$: C, 71.2; H, 9.4; N, 4.4. Found: C, 71.4; H, 9.1; N, 4.2.

EXAMPLE 6 alpha,alpha'-(Di-1-benzyloxy-2,2,6,6-tetramethylpiperidin-4-yloxy)-p-xylene

A mixture of 27.7 g (61.7 mmol) of alpha,alpha'-(di-1-hydroxy-2,2,6,6-tetramethylpiperidine-4-yloxy)-p-xylene, 4.44 g (18.5 mmol) of 97% sodium hydride and 200 ml of tetrahydrofuran is gently refluxed until hydrogen evolution ceases. Benzyl bromide 31.6 g (185 mmol) is then added dropwise, and the reaction mixture is heated at reflux for 3 hours, then stirred overnight at room temperature. Excess sodium hydride is decomposed with methanol. Toluene (500 ml) is added, and the reaction mixture is filtered to remove salts. The filtrate is washed with water (3 × 1000 ml) and saturated sodium chloride (500 ml), then dried over magnesium sulfate and concentrated to give an oil. The oil is crystallized from methanol to give 29.7 g (77% yield) of a white solid, m.p. 126°–29° C.

Anal. Calcd. for $C_{40}H_{56}N_2O_4$: C, 76.4; H, 9.0; N, 4.5. Found: C, 76.0; H, 9.1; N, 4.4.

EXAMPLE 7

Di-(1-benzyloxy-2,2,6,6-tetramethylpiperidin-4-yl) Sebacate

A solution of 40.0 g (83 mmol) of di-(2,2,6,6-tetramethylpiperidin-4-yl) sebacate in 130 ml of toluene is warmed to 80° C. Molybdenum hexacarbonyl (1.0 g) is added and a solution of 5.0M t-butyl hydroperoxide (266 ml, 1.33 mmol) is also added over 15 minutes. The reaction mixture is irradiated for 24 hr. with a UV lamp while the internal temperature is maintained at 85°–90° C. The reaction mixture is filtered and the filtrate is evaporated until the volume is approximately 100 ml. The solution is chromatographed on silica gel (9:1 heptane: ethyl acetate) to obtain an oil which is crystallized from methanol. Recrystallization from ethanol gives 16.8 g (29% yield) of a white solid, mp 64°–68° C.

Anal. Calcd. for $C_{42}H_{64}N_2O_6$: C, 72.8; H, 9.3; N, 4.0. Found: C, 72.7, H, 9.2; N, 4.0.

EXAMPLE 8

Di-(1-benzyloxy-2,2,6,6-tetramethylpiperidin-4-yl) Phthalate

The compound is prepared according to the procedure given in Example 7, except that molybdenum hexacarbonyl is added prior to heating the reaction mixture. mp 141°–43° C.

Anal. Calcd. for $C_{40}H_{52}N_2O_6$: C, 73.1; H, 8.0; N, 4.3. Found: C, 73.0, H, 7.7; N, 4.2.

EXAMPLE 9

Di-(1-benzyloxy-2,2,6,6-tetramethylpiperidin-4-yl) Isophthalate

A mixture of 35.0 g (78.7 mmol) of di-(2,2,6,6-tetramethylpiperidin-4-yl) isophthalate, 1.0 g of molybdenum hexacarbonyl, and 75 ml of toluene is heated to 90° C. in a nitrogen atmosphere. A solution of 4.2M t-butyl hydroperoxide in toluene (225 ml, 945 mmol) is added over 5 min. The reaction mixture turns red. After the addition, the reaction mixture is irradiated for 6 hours (internal temp. 85° C.) with a UV lamp. Another 1.0 g portion of molybdenum hexacarbonyl is added, and the reaction mixture is irradiated for 16 hours. The mixture is then filtered and concentrated. The crude residue is chromatographed on silica gel (9:1 hexane: ethyl acetate). The less polar of the two major products is recrystallized from 9:1 ethanol:dichloromethane to obtain 14.8 g (29% yield) of a white solid, mp 135°–141° C., which is the title compound.

Anal. Calcd. for $C_{40}H_{52}N_2O_6$: C, 73.1; H, 8.0; N, 4.3. Found: C, 72.9; H, 7.7; N, 4.6.

EXAMPLE 10

Di-(1-benzyloxy-2,2,6,6-tetramethylpiperidin-4-yl) Diethylmalonate

The compound is prepared from di-(2,2,6,6-tetramethylpiperidin-4-yl) diethylmalonate, t-butylhydroperoxide, toluene, and molybdenum hexacarbonyl according to the procedure given in Example 8. mp 122°-23° C.

Anal. Calcd. for $C_{39}H_{58}H_2O_6$: C, 72.0; H, 9.0; N, 4.3. Found: C, 72.0; H, 9.3; N, 4.7.

EXAMPLE 11

Di-[1-(alpha-methylbenzyloxy)-2,2,6,6-tetramethylpiperidin-4-yl] Phthalate

The compound is prepared from 40.0 g of di-(1-oxyl-2,2,6,6-tetramethylpiperidin-4-yl) phthalate, 200 ml of ethylbenzene, and 2.0 g of molybdenum oxide which are heated to 110° C. (nitrogen atmosphere). Thereafter, 65 g of 70% t-butyl hydroxperoxide in water is added dropwise over one hour. The reaction mixture is refluxed for 3 hours after the hydroperoxide addition is complete. The crude product is chromatographed on silica gel (9:1 hexane: ethyl acetate) to give 51.0 g (88% yield) of a soft glassy product.

Anal. Calcd. for $C_{42}H_{56}N_2O_6$: C, 73.7; H, 8.2; N, 4.1. Found: C, 74.1; H, 8.4; N, 4.1.

EXAMPLE 12

Di-[1-(alpha-methylbenzyloxy)-2,2,6,6-tetramethylpiperidine-4-yl] Sebacate

A mixture of 40.0 g (83 mmol) of di-(2,2,6,6-tetramethylpiperidin-4-yl) sebacate, 2.0 g of molybdenum oxide, and 250 ml of ethylbenzene is heated to 110° C. (nitrogen atmosphere). A commercially available solution of 70% t-butyl hydroperoxide in water (64.3 g, 499 mmol) is added dropwise over 30 min. Water is collected in a Dean-Stark trap. Heating is continued for 90 minutes after the addition. The reaction mixture is filtered and evaporated. The resulting crude oil is dissolved in heptane (300 ml), and this solution is passed through a short column of silica gel. The first 350 ml of filtrate, nearly pure by TLC, is evaporated to give 41.7 g (70% yield) of the title compound, a viscous oil.

Anal. Calcd. for $C_{44}H_{68}N_2O_6$: C, 72.8; H, 9.6; N, 3.9. Found: C, 72.9; H, 9.7; N, 3.8.

EXAMPLE 13

Di-(1-heptyloxy-2,2,6,6-tetramethylpiperidin-4-yl) Sebacate

A mixture of 35.0 g (72.8 mmol) of di-(2,2,6,6-tetramethylpiperidin-4-yl) sebacate, 58.3 (582 mmol) of 90% aqueous t-butyl hydroperoxide, 2.0 g of molybdenum trioxide, and 250 ml of heptane is heated at 140° C. in a Fischer-Porter bottle. The pressure is maintained at 40-50 psi by occasional venting. Heating is discontinued after 7 hours. An additional portion (20.0 g) of 90% t-butyl hydroperoxide is added and the reaction mixture is heated for one hour at 140° C. The reaction is nearly colorless by this time. The reaction mixture is cooled and filtered to remove the catalyst. The organic phase is separated, dried over magnesium sulfate, and concentrated to 100 ml total volume. This solution is passed through silica gel with heptane as the eluent. The filtrate is evaporated to yield 36.9 g (72% yield) of the title compound, a nearly colorless oil.

Anal. Calcd. for $C_{42}H_{80}N_2O_6$: C 71.1; H 11.4; N 3.95. Found: C 71.3; H 11.8; N 3.9.

EXAMPLE 14

Di-(1-alpha-methylbenzyloxy-2,2,6,6-tetramethylpiperidin-4-yl) Terephthalate A suspension of 40.0 g (90.0 mmol) of di-(2,2,6,6-tetramethylpiperidin-4-yl) terephthalate, 2.0 g of molybdenum trioxide, and 250 ml of ethylbenzene is heated to 110° C. t-Butyl hydroperoxide (70%, 69.5 g, 540 mmol) is rapidly added. No reaction is visible until water is removed by azeotropic distillation and the internal temperature reaches 115° C. Heating is continued for 6 hours. The nearly colorless reaction mixture is allowed to cool, then filtered and evaporated to yield a pink solid. The solid is recrystallized (9:1 2-propanol: methylene chloride) to yield 48.4 g of the title compound, a white solid, m.p. 150°-152° C. A second crop of 5.3 g is obtained from the mother liquor. Total yield 53.7 g (87% yield).

Anal. Calcd. for $C_{42}H_{56}N_2O_6$: C, 73.7; H, 8.2; N, 4.1. Found: C, 74.0; H, 8.2; N, 4.0.

EXAMPLE 15

Di-(1-alpha-methylbenzyloxy-2,2,6,6-tetramethylpiperidin-4-yl) Isophthalate

A mixture of 40.0 g (90.0 mmol) of di-(2,2,6,6-tetramethylpiperidin-4-yl) isophthalate, 2.0 g of molybdenum trioxide, and 250 ml of ethylbenzene is heated to 110° C. t-Butyl hydroperoxide (70%, 69.5 g, 540 mmol) is added dropwise over a 45 min. period. The reaction mixture turns red during the addition. Water is removed by azeotropic distillation. The mixture is refluxed for 4 hours after the addition is complete. The catalyst is filtered, and the filtrate is evaporated to obtain a yellow oil. A kugelrohr distillation (110° C., 0.1 mm Hg) is performed to remove volatile by-products. The residue, a viscous oil, is dissolved in hexane and passed through silica gel. Evaporation yields a crude solid which is recrystallized from ethanol to yield 39.8 g (65% yield) of the title compound, a white powder, m.p. 118°-34° C.

Anal Calcd for $C_{42}H_{56}N_2O_6$: C, 73.7; H, 8.2; N, 4.1. Found: C, 73.4; H, 8.3; N, 4.1.

EXAMPLE 16

Di-(1-ethoxy-2,2,6,6-tetramethylpiperidin-4-yl) Sebacate

A solution of 7.8 g (32.5 mmol) of sebacoyl chloride in 20 ml of dichloromethane is added dropwise over 15 min. to a solution of 13.1 g (65.1 mmol) of 1-ethoxy-4-hydroxy-2,2,6,6-tetramethylpiperidine, 7.0 g of triethylamine and 100 ml of dichloromethane. The reaction mixture begins to reflux during the addition. The reaction is gently refluxed for an additional hour. Ether (500 ml) is added, the precipitate filtered and the filtrate washed with 1N HCl (2×100 ml), water (200 ml), and saturated sodium bicarbonate (300 ml). The organic solution is dried over magnesium sulfate and evaporated to obtain an oil. Purification by chromatography (silica gel, 19:1 hexane:ethyl acetate) affords 12.7 g (69% yield) of the title compound, a colorless oil.

Anal. Calcd. for $C_{32}H_{50}N_2O_6$: C, 67.6; H, 10.6; N, 4.9. Found: C, 67.3, H, 10.8, N, 4.8.

EXAMPLE 17

Di-(1-cumyloxy-2,2,6,6-tetramethylpiperidin-4-yl) Sebacate

The title compound is prepared according to the procedure in Example 16 except that the 1-cumyloxy reactant is utilized. The reaction temperature reaches 33° C. during the addtion, and the reaction mixture is then stirred for 1 hour at ambient temperature. The product is a white solid, m.p. 94°–6° C.

Anal. Calcd. for $C_{46}H_{72}N_2O_6$: C, 73.76; H, 9.69; N, 3.74. Found: C, 74.0; H, 9.8; N, 3.8.

EXAMPLE 18

8-alpha-Methylbenzyloxy-7,7,9,9-tetramethyl-8-aza-1,4-dioxaspiro[4.5]decane

A mixture of 38.1 g (191 mmol) of 7,7,9,9-tetramethyl-8-aza-1,4-dioxaspiro[4.5]decane, 73.8 g (574 mmol) of 70% aq. t-butyl hydroperoxide, 2.0 g of molybdenum trioxide, and 130 ml of ethylbenzene is refluxed for 6 hours. Water is collected in a Dean-Stark trap. The catalyst is filtered and the filtrate is concentrated at reduced pressure. The residue is dissolved in heptane and passed through silica gel. A Kugelrohr distillation (120° C., 0.1 mm Hg) is used to remove volatile by-products. The title compound crystallizes on standing.

Anal. Calcd. for $C_{19}H_{29}NO_3$: C, 71.4; H, 9.1; N, 4.4. Found: C, 70.3; H, 9.2; N, 4.4.

EXAMPLE 19

3,15-Di-alpha-methylbenzyloxy-2,2,4,4,14,14,16,16-octamethyl-7,11,18,21-tetraoxa-3,15-diazatrispiro[5.2.2.5.2.2.]heneicosane The title compound is prepared from 2,2,4,4,14,14,16,16-octamethyl-7,11,18,21-tetraoxa-3,15-diazatrispiro[5.2.2.5.2.2]heneicosane according to the procedure given in Example 18. The catalyst is filtered and the filtrate is concentrated to yield an oil which is crystallized from ethanol to give 19.6 g (65% yield) of a white powder, m.p. 150°–53° C.

EXAMPLE 20

3,15-Dicyclohexyloxy-2,2,4,4,,14,14,16,16-octamethyl-7,11,18,21-tetraoxa-3,15-diazatrispiro[5.2.2.5.2.2.-]heneicosane A mixture of 16.7 g (37.9 mmol) of 3,15-dioxyl-2,2,4,4,14,14,16,16-octamethyl-7,11,18,21-tetraoxa-3,15-diazatrispiro[5.2.2.5.2.2.]heneicosane, 22.8 g (227 mmol) of 90% aq. t-butyl hydroperoxide, 2.0 g of molybdenum trioxide, and 125 ml of cyclohexane is heated in a Fischer-Porter bottle at 155°–160° C. (bath temperature) for 6 hours. The pressure is maintained at 40–50 psi by occasional venting. The catalyst is filtered and the filtrate is concentrated. The residue is dissolved in hexane and passed through silica gel. Crystallization from 2-propanol yields 8.0 g (35%) of a white solid, m.p. 163°–175° C.

Anal. Calcd. for $C_{35}H_{62}N_2O_6$: C, 69.3; H, 10.3; N, 4.6. Found: C, 68.7; H, 10.3; N, 4.7.

EXAMPLE 21

Di-(1-methoxy-2,2,6,6-tetramethylpiperidin-4-yl) n-Butylmalonate

A mixture of diethyl n-butylmalonate (11.55 g, 53.4 mmol), 4-hydroxy-1-methoxy-2,2,6,6-tetramethylpiperidine (20.0 g, 107 mmol), lithium amide (120 mg), and xylene (100 ml) is distilled until the distillate reaches a constant temperature of 137° C. Xylene is evaporated and the residue is dissolved in heptane. Acetic acid is added and the resulting precipitate is filtered. The filtrate is concentrated to obtain 26.2 g (98% yield) of a light yellow oil.

Anal Calcd for $C_{27}H_{50}N_2O_6$: C, 65.0; H, 10.1; N, 5.6. Found: C, 65.0; H, 10.4; N, 5.5.

EXAMPLE 22

Di-(1-methoxy-2,2,6,6-tetramethylpiperidin-4-yl) (3,5-Di-t-butyl-4-hydroxybenzyl)-n-butylmalonate A mixture of 11.9 g (45.2 mmol) of N,N-dimethyl-3,5-di-t-butyl-4-hydroxybenzylamine, 18.8 g (37.7 mmol) of di-(1-methoxy-2,2,6,6-tetramethylpiperidin-4-yl) n-butylmalonate, 173 mg of lithium amide, and 100 ml of tetrahydrofuran is refluxed for 90 minutes. The reaction mixture is diluted with ethyl acetate (350 ml). The organic solution is washed with 1N HCl (2×100 ml), water (2×250 ml), and saturated $NaHCO_3$ solution (250 ml), then dried over magnesium sulfate and evaporated to obtain a brown oil. Crystallization from 9:1 methanol:water affords 14.9 g (55% yield) of a white solid (mp 111°–13° C.).

Anal. Calcd. for $C_{42}H_{72}N_2O_7$: C, 70.3; H, 10.1; N, 3.9. Found: C, 70.2; H, 10.2; N, 3.9.

EXAMPLE 23

Di-(1-cyclohexyloxy-2,2,6,6-tetramethylpiperidin-4-yl) n-Butylmalonate

The title compound, a viscous oil, is prepared in 89% yield following the procedure given in Example 21 utilizing the 1-cyclohexyloxy starting material.

Anal. Calcd. for $C_{37}H_{66}N_2O_6$: C, 70.0; H, 10.5; N, 4.4. Found: C, 69.8; H, 10.7; N, 4.4.

EXAMPLE 24

Di-(1-cyclohexyloxy-2,2,6,6-tetramethylpiperidin-4-yl) (3,5-Di-t-butyl-4-hydroxybenzyl)-n-butylmalonate The title compound, a white crystalline solid, is prepared in 80% yield following the procedure given in Example 22 utilizing the 1-cyclohexyloxy material, m.p. 184°–5° C. (ethyl acetate).

Anal. Calcd. for $C_{52}H_{88}N_2O_7$: C, 73.2; H, 10.4; N, 3.3. Found: C, 73.7; H, 10.8, N, 3.3.

EXAMPLE 25

Poly-{[6-(1,1,3,3-tetramethylbutyl)-imino]-1,3,5-triazine-2,4-diyl][2-(1-cyclohexyloxy-2,2,6,6-tetramethylpiperidyl)-imino]-hexamethylene-[4-(1-cyclohexyloxy-2,2,6,6-tetramethylpiperidyl)-imino]}

A mixture of 46.9 g of the N-oxyl precursor, 40.2 g (402 mmol) of 90% t-butyl hydroperoxide, 6.0 g of molybdenum oxide, and 200 ml of cyclohexane is heated for 3 hours at 155° C. under pressure. The colorless reaction mixture is diluted with a mixture of ether, methylene chloride, and toluene, and filtered. The filtrate is stirred with 5% aqueous sodium sulfite (400 ml) for 45 minutes. The organic phase is washed with water, dried with magnesium sulfate, and filtered. After the filtrate is concentrated, methanol is added to precipitate the product. The yield is 19.2 g (36%) of a white powder, m.p. 187°–200° C.

Anal. Calcd. for $(C_{47}H_{86}N_8O_2)_n$: C, 71.0; H, 10.9; N, 14.1. Found: C, 68.2; H, 10.6; N, 14.0.

EXAMPLE 26

1-Methoxy-2,2,6,6-tetramethylpiperidin-4-yl 3,5-Di-t-butyl-4-hydroxybenzoate A solution of 7.6 g (28.3 mmol) of 3,5-di-t-butyl-4-hydroxybenzoyl chloride in toluene (35 ml) is added dropwise over 20 minutes to a solution of 5.3 g (28.3 mmol) of 4-hydroxy-1-methoxy-2,2,6,6-tetramethylpiperidine and 2.46 g (31.1 mmol) of pyridine in toluene (30 ml). The reaction temperature is kept below 60° C. during the addition and the reaction mixture is stirred for one hour at 55°–60° C. after the addition and then filtered. The filtrate is washed with 1N HCl (2×50 ml), water (100 ml), saturated NaHCO3 (100 ml), dried (magnesium sulfate), and concentrated. The crude oil is chromatographed on silica gel (9:1 hexane:ethyl acetate) to obtain 7.3 g (61% yield of a white crystalline solid, m.p. 126°–8° C. (methanol).

Anal. Calcd. for $C_{25}H_{41}NO_4$: C, 71.6; H, 9.8; N, 3.3. Found: C, 71.4; H, 9.9; N, 3.3.

EXAMPLE 27

1-Cyclohexyloxy-2,2,6,6-tetramethylpiperidin-4-yl-3,5-Di-t-butyl-4-hydroxybenzoate The title compound, a white solid, is prepared in 86% yield following the procedure given in Example 26 utilizing the 1-cyclohexyloxy material, mp 131°–2° C. (ethanol).

Anal. Calcd. for $C_{30}H_{49}NO_4$: C, 73.9; H, 10.1; N, 2.9. Found: C, 74.2; H, 10.0; N, 2.9.

EXAMPLE 28

Di-(1-cyclohexyloxy-2,2,6,6-tetramethylpiperidin-4-yl) Succinate

A two-phase mixture of 70% aqueous t-butyl hydroperoxide (103.9 g, 807 mmol), cyclohexane (200 ml) and sodium chloride (15 g) is shaken in a separatory funnel. The organic phase is dried over magnesium sulfate, filtered, and added to 40.0 g (101 mmol) of di-(2,2,6,6-tetramethylpiperidin-4-yl) succinate. Molybdenum oxide (2.0 g) is added, and the mixture is refluxed for one hour. Water is collected in a Dean-Stark trap. The entire reaction mixture is then transferred to a Fischer-Porter bottle and heated at 140° C. for 6 hours. Additional t-butyl hydroperoxide (90%, 10.1 g, 101 mmol) is added and heating is resumed for another 4 hours. The colorless reaction mixture is filtered, concentrated, and dissolved in heptane (20 0 ml). The heptane solution is passed through a short column of silica gel with heptane. Subsequent evaporation affords an oil which is crystallized from ethanol to yield 41.2 g (69%) of a white powder, m.p. 122°–6° C.

Anal. Calcd. for $C_{34}H_{60}N_2O_6$: C, 68.9; H, 10.2; N, 4.7. Found: C, 68.4; H, 10.5; N, 4.5.

EXAMPLE 29

Di-(1-alpha-methylbenzyloxy-2,2,6,6-tetramethyl-piperidin-4-yl) Succinate

The title compound is prepared following the procedure given in Example 15 utilizing the succinate starting material. Crystallization from ethanol affords a 78% yield of a white solid, mp 85°–88° C.

Anal. Calcd. for $C_{38}H_{56}N_2O_6$: C, 71.7; H, 8.9; N, 4.4. Found: C, 71.5; H, 8.6; N, 4.3.

EXAMPLE 30

Di-(1-nonyloxy-2,2,6,6-tetramethylpiperidin-4-yl) Sebacate

The title compound is prepared following the procedure given in Example 28 using the sebacate starting material and nonane, except that the reaction mixture is refluxed for 22 hours at atmospheric pressure. The crude product is passed through a short column of silica gel with heptane as the eluent to obtain a 73% yield of a colorless oil.

Anal. Calcd. for $C_{46}H_{88}N_2O_6$: C, 72.2; H, 11.6; N, 3.7. Found: C, 71.6; H, 11.5; N, 4.7.

EXAMPLE 31

Di-(1-octadecyloxy-2,2,6,6-tetramethylpiperidin-4-yl) Sebacate

The reaction is run in a Fischer-Porter bottle in a nitrogen atmosphere. The reaction vessel is charged with 15.0 g (31.2 mmol) of di-(2,2,6,6-tetramethylpiperidin-4-yl) sebacate, 101 g of octadecane, 25.3 g (253 mmol) of 90% t-butyl hydroperoxide, and 1.25 g of molybdenum trioxide. The Fischer-Porter bottle is placed in an oil bath and the bath temperature is brought to 143° C. over 1.3 hours. Heating is continued another 3.2 hours at 145±3° C. The colorless reaction mixture is cooled to room temperature, diluted with hexane (100 ml), and filtered to remove solids. The solids are rinsed with hexane (2×50 ml). The organic solution is stirred for 90 minutes with 16.1 g sodium sulfite in 200 ml of water to decompose unreacted hydroperoxide. Ethyl acetate is added (200 ml), and the organic solution is washed with water (4×250 ml), dried over magnesium sulfate, and concentrated to obtain 121 g of a colorless oil. The crude material is purified by flash chromatography (silica gel; heptane; then 20:1 heptane:ethyl acetate) to afford 20.8 g (66% yield) of the title compound as a colorless oil.

Anal. Calcd. for $C_{64}H_{124}N_2O_6$: C, 75.5; H, 12.3; N, 2.75. Found: C, 75.1; H, 12.6; N, 3.2.

EXAMPLE 32

Di-(1-cyclohexyloxy-2,2,6,6-tetramethylpiperidin-4-yl) Phthalate

A mixture of 30.0 g (67.5 mmol) of di-(2,2,6,6-tetramethyl-piperidin-4-yl) phthalate, 27.5 g (214 mmol) of 70% aqueous t-butyl hydroperoxide, 2.0 g of molybdenum trioxide, and 200 ml of cyclohexane is heated to reflux. Water is collected in a Dean-Stark trap. After 75 min., the reaction mixture becomes red. Another portion of t-butyl hydroperoxide (42.5 g, 70%, 330 mmol) is added over 30 minutes. After the additional water is collected, the reaction mixture is transferred to a Fischer-Porter bottle and heated at 140° C. for 4.5 hours. The nearly colorless reaction mixture is treated with 6.9 g (90%, 69 mmol) of t-butyl hydroperoxide and heated at 140° C. for 90 minutes to remove the last traces of pink color. The reaction mixture is cooled, filtered, and stirred with a solution of 43 g of sodium sulfite in 530 ml of water for 2 hours. Dichloromethane (600 ml) is added, and the organic layer is separated, dried over magnesium sulfate, and concentrated to obtain a crude solid. Purification (Waters Prep. 500A HPLC, 25:1 heptane:ethyl acetate) affords 31.0 g (72% yield) of a white solid, m.p. 149°–51° C.

Anal. Calcd. for $C_{38}H_{60}N_2O_6$: C, 71.2; H, 9.2; N, 4.4. Found: C, 71.1; H, 9.3; N, 4.3.

EXAMPLE 33

(1-Cyclohexyloxy-2,2,6,6-tetramethylpiperidine-4-yl)(1-Methoxy-2,2,6,6-tetramethylpiperidin-4-yl)Phthalate The title compound, a glass, is obtained as a by-product in Example 32.

Mass spec.: M+ = 572

EXAMPLE 34

1-Cyclohexyloxy-4-octadecanoyloxy-2,2,6,6-tetramethylpiperidine

The title compound is prepared in 69% yield from the reaction of octadecanoyl chloride with 1-cyclohexyloxy-4-hydroxy-2,2,6,6-tetramethylpiperidine following the procedure in Example 17. Purification (Waters Prep. 500A HPLC, 100:1 heptane:ethyl acetate) yields a white solid, m.p. 44°–47° C.

Anal Calcd. for $C_{33}H_{63}NO_3$: C, 76.0; H, 12.2; N, 2.7. Found: C, 76.8; H, 12.2; N, 2.7.

EXAMPLE 35

1-Cyclohexyloxy-4-(n-dodecylamino)-2,2,6,6-tetramethylpiperidine

Acetic acid (22.0 g, 367 mmol) is added dropwise to a solution of 15.0 g (59.2 mmol) of 1-cyclohexyloxy-2,2,6,6-tetramethylpiperidin-4-one and 54.9 g (296 mmol) of dodecylamine in 200 ml of dry tetrahydrofuran containing 5A molecular sieves (25 g). The reaction mixture warms during the addition. The mixture is then diluted with tetrahydrofuran (150 ml) and cooled to 21° C. Sodium cyanoborohydride (4.46 g, 7.1 mmol) is added in one portion. The reaction mixture is stirred at room temperature for 4 hours, then filtered. The filtrate is concentrated and the residue is partitioned between ether (400 ml) and 5% sodium hydroxide (250 ml). The organic layer is dried over magnesium sulfate, filtered, and concentrated. Residual dodecylamine is removed by Kugelrohr distillation (110° C., 0.3 mm). The crude product is purified by chromatography (silica gel) to afford 20.4 g (82% yield) of the title compound, as a nearly colorless oil.

Anal. Calcd. for $C_{27}H_{54}N_2O$: C, 76.7; H, 12.9; N, 6.6. Found: C, 76.7; H, 13.2; N, 6.7.

EXAMPLE 36

1-alpha-Methylbenzyloxy-4-(n-dodecylamino)-2,2,6,6-tetramethylpiperidine

The title compound, a colorless oil, is prepared from 1-alpha-methylbenzyloxy-2,2,6,6-tetramethylpiperidin-4-one and dodecylamine according to the procedure given in Example 35.

Anal. Calcd. for $C_{29}H_{52}N_2O$: C, 78.3; H, 11.8; N, 6.3. Found: C, 77.7; H, 11.6; N, 6.6.

EXAMPLE 37

1-alpha-Methylbenzyloxy-4-(n-butylamino)-2,2,6,6-tetramethylpiperidine

The title compound, a colorless oil, is prepared from 1-alpha-methylbenzyloxy-2,2,6,6-tetramethylpiperidine-4-one and butylamine according to the procedure given in Example 35 except that acetonitrile is substituted for tetrahydrofuran and the molecular sieves are omitted.

Anal. Calcd. for $C_{21}H_{36}N_2O$: C, 75.8; H, 10.9; N, 8.4. Found: C, 74.7; H, 11.0; N, 8.6.

EXAMPLE 38

N,N'-Di-(1-cyclohexyloxy-2,2,6,6-tetramethylpiperidin-4-yl)-1,6-hexanediamine

A mixture of 15.0 g (59.1 mmol) of 1-cyclohexyloxy-2,2,6,6-tetramethylpiperidin-4-one, 3.4 g (29.6 mmol) of 1,6-hexanediamine, 500 mg of platinum oxide, and 150 ml of ethanol is hydrogenated in a Paar apparatus for 4 hours. The catalyst is removed by filtration. The filtrate is concentrated to an oil which is purified by flash chromatography (silica gel:ethyl acetate, then ethyl acetate:methanol) to afford 9.7 g (55% yield) of the title compound, as a yellow oil.

Anal. Calcd. for $C_{36}H_{70}N_4O_2$: C, 73.2; H, 11.9; N, 9.5. Found: C, 72.7; H, 12.1; N, 9.3.

EXAMPLE 39

1-Cyclohexyloxy-4-(n-butylamino)-2,2,6,6-tetramethylpiperidine

The title compound, a colorless oil, is prepared from 1-cyclohexyloxy-2,2,6,6-tetramethylpiperidin-4-one and butylamine according to the procedure given in Example 38.

Anal Calcd. for $C_{19}H_{38}N_2O$: C, 73.5; H, 12.3; N, 9.0. Found: C, 73.0; H, 12.6; N, 8.6.

EXAMPLE 40

Di-(1-nonyloxy-2,2,6,6-tetramethylpiperidin-4-yl) Succinate

The title compound, a light yellow oil, is prepared from di-(2,2,6,6-tetramethylpiperidin-4-yl) succinate and nonane according to the procedure given in Example 30.

Anal. Calcd. for $C_{46}H_{76}N_2O_6$: C, 70.5; H, 11.2; N, 4.1. Found: C, 70.6; H, 11.3; N, 4.0.

EXAMPLE 41

Di-(1-decyloxy-2,2,6,6-tetramethylpiperidin-4-yl) Sebacate t-Butyl hydroperoxide (55.0 g of a 70% aqueous solution, 427 mmol) is added dropwise over 15 minutes to a mixture of 25.0 g (52.0 mmol) of di-(2,2,6,6-tetramethylpiperidin-4-yl) sebacate, 1.5 g (10.4 mmol) of molybdenum trioxide, and 225 ml of n-decane which has been heated to 90° C. The reaction mixture is refluxed for 7.5 hours, and water is collected in a Dean-Stark trap. The reaction mixture is cooled to room temperature, and then stirred for 2 hours with a solution of 26 g of sodium sulfite in 500 ml of water. The reaction mixture is diluted with ethyl acetate (200 ml). The organic layer is dried over magnesium sulfate and concentrated to an oil. The crude product is purified by flash chromatography (silica gel; 97:3 heptane:ethyl acetate) to afford 29.2 g (71% yield) of the title compound, as a colorless oil.

Anal Calcd for $C_{48}H_{92}N_2O_6$: C, 72.7; H, 11.7; N, 3.5. Found: C, 73.1; H, 12.2; N, 3.5.

EXAMPLE 42

Di-(1-dodecyloxy-2,2,6,6-tetramethylpiperidin-4-yl) Sebacate

The title compound, a colorless oil, is prepared from di-(2,2,6,6-tetramethylpiperidin-4-yl) sebacate and n-dodecane according to the procedure given in Example 41.

Anal. Calcd. for $C_{52}H_{100}N_2O_6$: C, 73.5; H, 11.9; N, 3.3. Found: C, 73.2; H, 12.2; N, 3.2.

EXAMPLE 43

4-Benzoyloxy-1-(1'-methylcyclohexyloxy)-2,2,6,6-tetramethylpiperidine t-Butyl hydroperoxide (70%, 65.2 g, 507 mmol), methylcyclohexane (150 ml), and sodium chloride (10 g) are agitated in a separatory funnel. The organic layer is dried over magnesium sulfate. The t-butyl hydroperoxidemethylcyclohexane solution is mixed with 35.0 g (127 mmol) of 4-benzoyloxy-1-oxyl-2,2,6,6-tetramethylpiperidine, 2.0 g of molybdenum trioxide, and 50 ml of methylcyclohexane. The reaction mixture is heated at reflux for 5 hours, then cooled to room temperature, filtered, and concentrated at reduced pressure. The crude product is diluted with heptane and passed through a short column of silica gel with heptane as the eluent to afford, after evaporation of solvent, 42.4 g (89% yield) of a clear colorless oil.

Anal. Calcd. for $C_{23}H_{35}NO_3$: C, 74.0; H, 9.4; N, 3.7. Found: C, 74.3; H, 9.8; N, 3.7.

EXAMPLE 44

Di-[1-(1-Methylcyclohexyloxy)-2,2,6,6-tetramethylpiperidin-4-yl] Sebacate t-Butyl hydroperoxide (70%, 133.9 g, 1.04 mol), methylcyclohexane (250 ml), and sodium chloride (20 g) are agitated in a separatory funnel. The organic layer is dried over magnesium sulfate. The t-butyl hydroperoxidemethylcyclohexane solution is mixed with 50.0 g (104 mmol) of di-(2,2,6,6-tetramethylpiperidin-4-yl) sebacate, 3.0 g of molybdenum trioxide, and 100 ml of methylcyclohexane. The reaction mixture is heated at reflux for 4.5 hours and water is collected in a Dean-Stark trap. The reaction is cooled to room temperature and filtered. The filtrate is concentrated at reduced pressure to obtain an oil which is purified by flash chromatography (silica gel; 19:1 heptane:ethyl acetate) to obtain 51.6 g (72% yield) of a colorless oil.

Anal. Calcd. for $C_{42}H_{76}N_2O_6$: C, 71.6; H, 10.9; N, 4.0. Found: C, 71.4; H, 11.0; N, 3.9.

EXAMPLE 45

Step A

4-Benzoyloxy-1-(2-cyclohexen-1-yloxy)-2,2,6,6-tetramethylpiperidine

A solution of 33.6 g (122 mmol) of 4-benzoyloxy-1-oxyl-2,2,6,6-tetramethylpiperidine, 23.0 g (157 mmol) of di-t-butyl peroxide, and 70 ml of cyclohexene is heated in a Fischer-Porter bottle at 138° C. for 6.5 hours. The reaction mixture is chromatographed on silica gel (200:1 heptane:ethyl acetate) to afford 35.1 g (81% yield) of a colorless oil.

Anal. Calcd. for $C_{22}H_{31}NO_3$: C, 73.9; H, 8.7; N, 3.9. Found: C, 73.7; H, 8.8; N, 3.9.

Step B 1-(2-Cyclohexen-1-yloxy)-4-hydroxy-2,2,6,6-tetramethylpiperidine

The title compound, a white solid (m.p. 66°-9° C.) is prepared by the hydrolysis (KOH-water-methanol) of 4-benzoyloxy-1-(2-cyclohexen-1-yloxy)-2,2,6,6-tetramethylpiperidine.

Anal. Calcd. for $C_{15}H_{27}NO_2$: C, 71.1; H, 10.7; N, 5.5. Found: C, 71.7; H, 11.4; N, 5.5.

Step C

Di-[1-(2-cyclohexen-1-yloxy)-2,2,6,6-tetramethylpiperidin-4-yl] Sebacate

The title compound, a colorless oil, is prepared from the reaction of 1-(2-cyclohexen-1-yloxy)-4-hydroxy-2,2,6,6-tetramethylpiperidine and sebacoyl chloride according to the procedure given in Example 17.

Anal. Calcd. for $C_{40}H_{68}N_2O_6$: C, 71.4; H, 10.2; N, 4.2. Found: C, 71.6; H, 10.7; N, 4.0.

EXAMPLE 46

Step A

4-Benzoyloxy-1-t-butoxy-2,2,6,6-tetramethylpiperidine

A solution of 56.0 g (203 mmol) of 4-benzoyloxy-1-oxyl-2,2,6,6-tetramethylpiperidine, 125 ml of chlorobenzene, and 58.9 g of t-butyl iodide is cooled to 5° C. Tri-n-butyltin hydride (29 g, 100 mmol) is added dropwise over 110 minutes while the temperature is maintained below 20° C. The reaction mixture is concentrated at reduced pressure and then purified by silica gel chromatography (200:1, then 100:3 heptane:ethyl acetate) to afford 30.1 g of a white solid, m.p. 80°-82.5° C.

Anal. Calcd. for $C_{20}H_{31}NO_3$: C, 72.0; H, 9.4; N, 4.2. Found: C, 71.9; H, 9.6; N, 4.1.

Step B 1-t-Butoxy-4-hydroxy-2,2,6,6-tetramethylpiperidine

The title compound, a white solid (m.p. 115°-16° C.), is prepared by the hydrolysis (KOH-water-methanol) of 4-benzoyloxy-1-t-butoxy-2,2,6,6-tetramethylpiperidine.

Anal. Calcd. for $C_{13}H_{27}NO_2$: C, 68.1; H, 11.9; N, 6.1. Found: C, 68.5; H, 12.4; N, 6.1.

Step C

Di-(1-t-butoxy-2,2,6,6-tetramethylpiperidin-4-yl) Sebacate

The title compound, a white solid (m.p. 62°-3° C.), is prepared from the reaction of 1-t-butoxy-4-hydroxy-2,2,6,6-tetramethylpiperidine and sebacoyl chloride according to the procedure given in Example 17.

Anal. Calcd. for $C_{36}H_{68}N_2O_6$: C, 69.2; H, 11.0; N, 4.4. Found: C, 69.5; H, 11.3; N, 4.4.

EXAMPLE 47

4-Acetamido-1-cyclohexyloxy-2,2,6,6-tetramethylpiperidine

A stirred mixture of 10.0 g of 4-acetamido-2,2,6,6-tetramethylpiperidine-1-oxyl, 16 ml of 70% aqueous tert-butylhydroperoxide and 0.67 g of molybdenum trioxide in 75 ml of cyclohexane is heated under reflux in a flask fitted with a Dean-Stark apparatus. After 6 ml of water is collected, the reaction mixture is transferred to a Fisher Porter apparatus and heated at 140° C. and 30 psi for 4 hours. The decolorized reaction mixture is filtered and the filtrate is washed with water, aqueous sodium sulfite, brine, dried (MgSO₄) and concentrated to give 13.61 g of a white solid. Recrystallization from heptane affords 10.39 g of the title compound as a white crystalline solid, m.p. 140°-44° C.

Anal. Calcd. for $C_{17}H_{32}N_2O_2$: C, 68.9; H, 10.9; N, 9.5. Found: C, 68.6; H, 11.3; N, 9.3.

EXAMPLE 48

4-Amino-1-cyclohexyloxy-2,2,6,6-tetramethylpiperidine

A solution of 5.0 g of the acetamide from Example 47 in 7.5 ml of water and 7.5 ml of conc. hydrochloric acid is heated at reflux for 10 hours. The reaction mixture is then quenched with saturated sodium carbonate and extracted with ethyl acetate. The combined organic extracts are washed with water, brine, dried ($MgSO_4$) and evaporated to leave a light brown oil. Distillation (Kugelrohr, 140° C. @ 1.5 mm) affords the title compound as a clear colorless oil.

EXAMPLE 49

N,N'-Bis[1-cyclohexyloxy-2,2,6,6-tetramethylpiperidin-4yl] Succinamide

A mixture of 1-cyclohexyloxy-4-amino-2,2,6,6-tetramethylpiperidine (2.65 g), dimethyl succinate (1.46 g) and sodium methoxide (50 mg) is heated at 180°-190° C. for 4 hours. The crude product is recrystallized from ethanol/water to afford 1.38 g of the title compound as a white solid, m.p. 230°-34° C.

Calcd. for $C_{34}H_{62}N_4O_4 \cdot H_2O$: C, 67.1; H, 10.6; N, 9.2. Found: C, 66.8; H, 10.7; N, 9.1.

EXAMPLE 50

Bis(1-methoxy-2,2,6,6-tetramethylpiperidin-4-yl)succinate

A mixture of 20.00 g (107 mmol) of 4-hydroxy-1-methoxy-2,2,6,6-tetramethylpiperidine, 7.41 g (50.7 mmol) of dimethyl succinate, 0.08 g of lithium amide, and 100 ml of toluene is heated at reflux for 7 hours. Methanol is distilled from the reaction mixture along with some of the toluene. The reaction mixture is cooled and a solution of 0.21 g of glacial acetic acid in toluene is added. The precipitate is removed by filtration. The filtrate is concentrated to give an oil which is purified by HPLC (Waters Prep 500 A, 29:1 heptane: ethyl acetate) to afford 14.5 g (63%) of the title compound.

Anal. Calcd. for $C_{24}H_{44}N_2O_6$: C 63.1; H 9.7; N 6.1. Found: C 63.1; H 9.9; N 6.0.

EXAMPLE 51

Bis(1-octyloxy-2,2,6,6-tetramethylpiperidin-4-yl)succinate

A solution of 143.1 g (1.11 mol) of 70% aqueous t-butyl hydroperoxide is added over a four hour period to a refluxing mixture of 55.0 g (139 mmol) of bis(2,2,6,6-tetramethylpiperidin-4-yl)succinate, 1.0 g of molybdenum trioxide, and 350 ml of n-octane. The reaction mixture is heated at reflux for 16 hours after the addition is complete in order to discharge the red color. The mixture is filtered to remove solids. The filtrate is concentrated to obtain a residue which is purified by flash chromatography to afford 53.6 g (59% yield) of the title compound, a yellow oil.

Anal. Calcd. for $C_{38}H_{72}N_2O_6$: C 69.9; H 11.1; N 4.3. Found: C 70.0; H 11.7; N 4.4.

EXAMPLE 52

Bis(1-methoxy-2,2,6,6-tetramethylpiperidin-4-yl)terephthalate

A mixture of 7.36 g (16.6 mmol) of bis(2,2,6,6-tetramethylpiperidin-4-yl)terephthalate, 0.1 g of molybdenum trioxide, and 25 ml of chlorobenzene is heated to 130° C. in a nitrogen atmosphere. A solution of 40.2 g (132 mmol) of cumene hydroperoxide in chlorobenzene is added to the reaction mixture over one hour. A Dean-Stark trap is used to remove water from the reaction. The reaction is heated at reflux for 4 hours after the addition is complete, then cooled and filtered. The filtrate is concentrated and the residue purified by filtration through silica gel with 19:1 heptane: ethyl acetate as the eluent. Crystallization from methanol affords 5.0 g (60% yield) of the title compound, a white powder, m.p. 179°-81° C.

Anal. Calcd. for $C_{28}H_{44}N_2O_6$: C 66.6; H 8.8; N 5.5. Found: C 66.7; H 8.9; N 5.4.

EXAMPLE 53

1-methoxy-4-n-butylamino-2,2,6,6-tetramethylpiperidine

A mixture of 10.1 g (54.5 mmol) of 1-methoxy-2,2,6,6-tetramethylpiperidin-4-one, 27.9 g (382 mmol) of n-butyl amine, 100 ml of methanol, and 1.0 g of 5% platinum on carbon is hydrogenated (50 psi, 25° C.) for 5 hours. The catalyst is removed by filtration. Evaporation of the filtrate gives an oil which is purified by fractional distillation to afford 10.6 g (80% yield) of the title compound, a colorless oil, b.p. 93°-100° C. (0.25 mm).

Anal. Calcd. for $C_{14}H_{30}N_2O$: C 69.4; H 12.5; N 11.6. Found: C 68.4; H 12.2; N 11.2.

EXAMPLE 54

Bis[N-(1-cyclohexyloxy-2,2,6,6-tetramethylpiperidin-4-yl)-N-n-butyl]sebacamide

70% aq. t-butyl hydroperoxide (41.4 g, 321 mmol) is partitioned between 200 ml of cyclohexane and 50 ml of saturated sodium chloride. A mixture of the t-butyl hydroperoxide/cyclohexane solution, 19.0 g (32 mmol) of bis[N-(2,2,6,6-tetramethylpiperidin-4-yl)-N-n-butyl]sebacamide, and 0.4 g of molybdenum trioxide is heated in a Fischer-Porter pressure bottle at 150°-160° C. for 2 hours. The reaction mixture is filtered and the filtrate evaporated. The residual oil is purified by flash chromatography on silica gel (3:1 heptane: ethyl acetate). Crystallization from methanol affords 13.1 g (52% yield) of the title compound, a white solid, m.p. 124°-28° C.

Anal. Calcd. for $C_{48}H_{90}N_4O_4$: C 73.2; H 11.5; N 7.1. Found: C 72.7; H 11.7; N 7.0.

EXAMPLE 55

Bis[N-(1-octyloxy-2,2,6,6-tetramethylpiperidin-4-yl]-N-n-butyl]sebacamide

A solution of 70% aq. t-butyl hydroperoxide (33.0 g, 256 mmol) is saturated with sodium chloride and extracted with 200 ml of n-octane. A mixture of 19.0 g (32 mmol) of bis[N-(2,2,6,6-tetramethylpiperidin-4-yl)-N-n-butylamino]sebacamide, 0.2 g of molybdenum trioxide, and one-half of the t-butyl hydroperoxide/octane solution is heated at reflux for 30 minutes. Water is collected in a Dean-Stark trap. The remainder of the t-butyl hydroperoxide/octane solution is then added to the refluxing reaction mixture over 2 hours. The reaction mixture is heated at reflux an additional 4.5 hours, then treated with 20.0 g (155 mmol) of 70% aq. t-butyl hydroperoxide and heated at reflux for two more hours to discharge the red color. Solids are removed by filtration, and the filtrate is evaporated. Purification of the crude product by flash chromatography on silica gel (4:1 heptane:

ethyl acetate) affords 16.0 g (59% yield) of the title compound, a pale yellow oil.

Anal. Calcd. for $C_{52}H_{102}N_4O_4$: C 73.7; H 12.1; N 6.6. Found: C 74.0; H 12.0; N 6.5.

EXAMPLE 56

1,6-bis[N,N'-di-(1-cyclohexyloxy-2,2,6,6-tetramethylpiperidin-4-yl)-acetylamino]hexane A mixture of 8.0 g (16.7 mmol) of 1,6-bis[N,N'-di-(2,2,6,6-tetramethylpiperidin-4-yl)-acetylamino]hexane, 21.5 g (167 mmol) of 70% aqueous t-butyl hydroperoxide, 0.1 g of molybdenum trioxide, and 100 ml of cyclohexane is heated at reflux for two hours. Water is collected in a Dean-Stark trap. The red reaction mixture is transferred to a Fischer-Porter pressure bottle and heated at 150°-60° C. for one hour to discharge the red color. Solids are removed by filtration, and the filtrate is evaporated to give an oil. Trituration of the oil in methanol affords 8.4 g (74% yield) of the title compound, a white solid, m.p. 65°-72° C.

Anal. Calcd. for $C_{40}H_{74}N_4O_4$: C 71.2; H 11.1; N 8.3. Found: C 70.5; H 11.0; N 8.2.

EXAMPLE 57

Bis(1-cyclooctyloxy-2,2,6,6-tetramethylpiperidin-4-yl)sebacate

A mixture of 75 g (156 mmol) of bis(2,2,6,6-tetramethylpiperidin-4-yl)sebacate, 1.3 g of molybdenum trioxide, and 475 ml of cyclooctane is heated to 118° C. To this mixture is added 130 g (1.01 mol) of 70% aq. t-butyl hydroperoxide during a 5 hour period. The reaction mixture is maintained at reflux during the addition, and water is collected in a Dean-Stark trap. The red reaction mixture is heated for 7 hours after the addition to discharge the red color. Solids are removed by filtration, and the filtrate is evaporated to give a yellow oil. Purification (Waters Prep. 500 A HPLC, 20:1 hexane: ethyl acetate) affords 78.7 g (68%) of the title compound, a colorless syrup.

Anal. Calcd. for $C_{44}H_{80}N_2O_6$: C 72.1; H 11.0; N 3.8. Found: C 72.0; H 11.0; N 3.7.

EXAMPLE 58

Bis(1-octyloxy-2,2,6,6-tetramethylpiperidin-4-yl)sebacate

70% Aqueous t-butyl hydroperoxide (140 g, 1.09 mol) is added over a 6 hour period to a mixture of 75.4 g (0.157 mol) of bis(2,2,6,6-tetramethylpiperidin-4-yl)sebacate, 1.25 g (8.7 mmol) of molybdenum trioxide, and 570 ml of n-octane that has been heated to 115° C. under a nitrogen atmosphere. During the addition, the reaction is maintained at reflux. Water is collected in a Dean-Stark trap. Upon completion of the addition, the red reaction mixture is heated at reflux (95°-97° C.) for seven hours to discharge the red color. The molybdenum trioxide is removed by filtration. The yellow filtrate is stirred at ambient temperature for 30 minutes with 15 g of activated charcoal (DARCO) to remove some of the yellow color, and then concentrated at reduced pressure. The crude product is purified by flash chromatography on silica gel (100:3 heptane: ethyl acetate) to afford 92.9 g (80% yield) of the title compound, a colorless oil.

Anal. Calcd. for $C_{44}H_{84}N_2O_6$: C 71.7; H 11.5; N 3.8. Found: C 71.6; H 11.5; N 3.6.

EXAMPLE 59

Bis(1-heptyloxy-2,2,6,6-tetramethylpiperidin-4-yl)succinate

70% Aqueous t-butyl hydroperoxide (78.9 g, 0.613 mol) is added over a 30 minute period to a mixture of 55.0 g (0.139 mol) of bis(2,2,6,6-tetramethylpiperidin-4-yl)succinate, 1.0 g of molybdenum trioxide, and 400 ml of n-heptane maintained at 110° C. Water is collected in a Dean-Stark trap. After the addition is complete, the reaction mixture is heated at reflux for 30 minutes. Another portion of 70% aqueous t-butyl hydroperoxide (100 g, 0.777 mol) is added to the red reaction mixture over a 90 minute interval. The reaction is heated at reflux for 16 hours to discharge the red color. The molybdenum trioxide is removed by filtration, and the filtrate is evaporated at reduced pressure. The residue is purified by flash chromatography (19:1, then 9:1 heptane: ethyl acetate) on silica gel to afford 63.6 g (73% yield) of the title compound, a clear, yellow liquid.

Anal. Calcd. for $C_{36}H_{68}N_2O_6$: C 69.2; H 11.0; N 4.5. Found: C 68.8; H 11.1; N 4.5.

EXAMPLE 60

Bis(1-decahydronaphthalenyloxy-2,2,6,6-tetramethylpiperidin-4-yl)sebacate

A mixture of 25.0 g (0.052 mol) of bis(2,2,6,6-tetramethylpiperidin-4-yl)sebacate, 55.0 g (0.427 mol) of 70% aqueous t-butyl hydroperoxide, 1.5 g (0.010 mol) of molybdenum trioxide, and 180 ml of decahydronaphthalene is heated at reflux for 4.5 hours until the red color disappears. Water is collected in a Dean-Stark trap. The molybdenum trioxide is removed by filtration and the filtrate stirred with a solution of 26 g of sodium sulfite in 500 ml of water to decompose unreacted t-butyl hydroperoxide. The two-phase mixture is diluted with ethyl acetate (200 ml) and the organic layer washed with saturated sodium chloride, dried over magnesium sulfate, and concentrated at reduced pressure to obtain an oil. Purification by flash chromatography (silica gel, 19:1 heptane: ethyl acetate) affords 28.8 g (71% yield) of the title compound, a pale yellow oil.

Anal. Calcd. for $C_{48}H_{84}N_2O_6$: C 73.4; H 10.8; N 3.6. Found: C 74.9; H 11.5; N 3.4.

EXAMPLE 61

Bis(1-cyclododecyloxy-2,2,6,6-tetramethylpiperidin-4-yl)sebacate

A mixture of 30.1 g (62.6 mmol) of bis(2,2,6,6-tetramethylpiperidin-4-yl)sebacate, 44 g (439 mmol) of 90% t-butyl hydroperoxide, 0.5 g of molybdenum trioxide, and 207 g of cyclododecane is heated in a Fischer-Porter pressure bottle at 135°-145° C. for 7.5 hours. The reaction mixture is purified first by flash chromatography on silica gel (heptane, then 20:1 heptane: ethyl acetate) and then by HPLC (Waters Prep. 500 A, 25:1 hexane: ethyl acetate) to afford 36.3 g (69% yield) of the title compound, a white solid, m.p. 70°-78° C.

Anal. Calcd. for $C_{52}H_{96}N_2O_6$: C 73.9; H 11.5; N 3.3. Found: C 74.1; H 11.5; N 3.1.

EXAMPLE 62

N,N',N'',N'''-tetrakis)[2,4-bis[N-(1-cyclohexyloxy-2,2,6,6-tetramethylpiperidin-4-yl)-n-butylamino]-1,3,5-triazin-6-yl}-3,3'-ethylenediiminodipropylamine To a refluxing mixture of 30.0 g (13.8 mmol) of the hindered amine precursor (Chimassorb 905 from CIBA-GEIGY Corp.), 1.0 g of molybdenum trioxide, and 300 ml of cyclohexane is added 88.7 g (689 mmol) of 70% aqueous t-butyl hydroperoxide over a one hour period. The reaction mixture is heated at reflux for another hour after the addition is completed. Water and some organic distillate (100 ml) are collected in a Dean-Stark trap and removed from the reaction mixture. The reaction mixture is then transferred to a Fischer-Porter pressure bottle and heated for five hours at 130°–135° C. An additional portion of 70% t-butyl hydroperoxide (14.0 g, 107 mmol) is added to the mixture, and heating is resumed for three hours. The reaction mixture is cooled and solids are removed by filtration. The filtrate is concentrated, diluted with 19:1 heptane:ethyl acetate, and purified by flash chromatography on silica gel (19:1 heptane:ethyl acetate) to afford 24.0 g (59%) of the title compound, a pale yellow glass (glass softening point 108°–123° C.).

Anal. Calcd. for $C_{172}H_{314}N_{32}O_8$: C 69.8; H 10.7; N 15.1. Found: C 66.6; H 10.6; N 14.7.

EXAMPLE 63

2,4,6-tris[N-(1-cyclohexyloxy-2,2,6,6-tetramethylpiperidin-4-yl)-n-butylamino]-1,3,5-triazine To a refluxing mixture of 13.5 g (19.0 mmol) of 2,4,6-tris[N-(2,2,6,6-tetramethylpiperidin-4-yl)-n-butylamino]-1,3,5-triazine, 0.2 g of molybdenum trioxide, and 175 ml of cyclohexane are added 36.6 g (284 mmol) of 70% aqueous t-butyl hydroperoxide over a 10 minute interval. The red reaction mixture is heated at reflux for one hour and then transferred to a Fischer-Porter pressure bottle using 25 ml of fresh cyclohexane. The reaction mixture is then heated for 3 hours at 150° C. to discharge the red color. Solids are removed by filtration and the filtrate is concentrated to a residue which is purified by flash chromatography on silica gel (19:1 heptane:ethyl acetate). The product is crystallized from isopropyl alcohol to afford 7.6 g (40% yield) of a white powder, m.p. 189°–94° C.

Anal. Calcd. for $C_{60}H_{111}N_9O_3$: C 71.6; H 11.1; N 12.5. Found: C 71.8; H 11.1; N 12.6.

EXAMPLE 64

2,4-Bis[N-(1-cyclohexyloxy-2,2,6,6-tetramethylpiperidin-4-yl)-n-butylamino]-6-t-octylamino-1,3,5-triazine A mixture of 22.2 g (35.3 mmol) of 2,4-bis[N-2,2,6,6-tetramethylpiperidin-4-yl)-n-butylamino]-6-t-octylamino-1,3,5-triazine, 0.3 g of molybdenum trioxide, 35.3 g (353 mmol) of 90% aqueous t-butyl hydroperoxide, and 250 ml of cyclohexane is heated for five hours at 150°–55° C. in a Fischer-Porter pressure bottle. The pressure is kept below 45 psi by occasional venting. The mixture is then cooled and solids are removed by filtration. The filtrate contains two major products, which are separated by a combination of flash chromatography (39:1 heptane:ethyl acetate) and HPLC (Waters Prep 500 A, 99:1 heptane:ethyl acetate followed by ethyl acetate). The title compound is the more polar product, a pale yellow glass, m.p. 85°–103° C. The yield is 11 g (38%).

Anal. Calcd. for $C_{49}H_{92}N_8O_2$: C 71.3; H 11.2; N 13.6. Found: C 71.2; H 12.0; N 13.6.

EXAMPLE 65

2,4-Bis[N-(1-cyclohexyloxy-2,2,6,6-tetramethylpiperidin-4-yl)-n-butylamino]-6-morpholino-1,3,5-triazine A mixture of 10.0 g (13.7 mmol) of 2-chloro-4,6-bis[N-(1-cyclohexyloxy-2,2,6,6-tetramethylpiperidin-4-yl)-n-butylamino]-1,3,5-triazine (see Example 75), 1.43 g (16.4 mmol) of morpholine, 0.8 g of sodium hydroxide, and 30 g of toluene is heated at reflux for four hours. Water is collected in a Dean-Stark trap. The liquid phase is decanted and residual solids are washed with toluene. The combined organic solutions are dried over magnesium sulfate and concentrated to give a viscous oil. Purification by HPLC (Waters Prep. 500 A, 29:1 heptane:ethyl acetate) affords 5.9 g (55% yield) of the title compound, a white powder, m.p. 159°–63° C.

Anal. Calcd. for $C_{45}H_{82}N_8O_3$: C 69.0; H 10.6; N 14.3. Found: C 69.4; H 10.6; N 14.3.

EXAMPLE 66A 2,4-bis[N-(1-cyclohexyloxy-2,2,6,6-tetramethylpiperidin-4-yl)-n-butylamino]-6-diethylamino-1,3,5-triazine A mixture of 50.0 g (271 mmol) of cyanuric chloride, 22.0 g of 50% aqueous sodium hydroxide, 22 ml of water, and 150 ml of toluene, cooled to 0° C., is admixed with a solution of 19.8 g (271 mmol) of diethylamine in 25 ml of toluene over a 45 minute interval. The reaction temperature is maintained at 0°–5° C. throughout the addition. After the addition is complete, the reaction mixture is stirred for two hours at ambient temperature. Water is added to the mixture to dissolve the sodium chloride, and the phases are separated. The organic phase is dried over magnesium sulfate and concentrated to give an oil which is crystallized from heptane to give 42.0 g (70% yield) of 2,4-dichloro-6-diethylamino-1,3,5-triazine, a white crystalline material, m.p. 77°–9° C.

EXAMPLE 66B 4-n-Butylamino-2,2,6,6-tetramethylpiperidine (31.7 g, 149 mmol) is added over 15 minutes to a suspension of 15.0 g (67.8 mmol) of the 2,4-dichloro-6-diethylamino-1,3,5-triazine, 150 ml of xylene, and 7.0 g of powdered sodium hydroxide that had been heated to 70° C. The reaction mixture is heated at reflux for 23 hours. Sodium chloride is removed by filtration, and the filtrate is concentrated to a viscous oil. Further concentration of the oil by Kugelrohr distillation (140°–50° C., 0.05 mm) yields a residue which is crystallized from methanol-water to afford 25.8 g (66% yield) of 2,4-bis[N-(2,2,6,6-tetramethylpiperidin-4-yl)-n-butylamino]-6-diethylamino-1,3,5-triazine, m.p. 74°–76° C.

EXAMPLE 66C

A mixture of 14.0 g (24.4 mmol) of 2,4-bis[N-(2,2,6,6-tetramethylpiperidin-4-yl]-n-butylamino]-6-diethylamino-1,3,5-triazine, 31.4 g (244 mmol) of 70% aqueous t-butyl hydroperoxide, 0.15 g of molybdenum trioxide, and 140 ml of cyclohexane is heated at reflux for 3 hours. The red mixture is then transferred to a Fischer-Porter bottle and heated at 145°–55° C. for 3 hours to discharge the red color. Solids are removed by filtration and the filtrate is concentrated to give a residue which is purified by flash chromatography (39:1

EXAMPLE 67

N,N',N'',N'''-tetrakis{-2,4-bis[N-(1-octyloxy-2,2,6,6-tetramethylpiperidin-4-yl)-n-butylamino]-1,3,5-triazin-6-yl-}-3,3'-ethylenediiminodipropylamine 94.6 g (736 mmol) of 70% aqueous t-butyl hydroperoxide is extracted with 300 ml of n-octane. A mixture of 100 ml of the t-butyl hydroperoxide/octane solution, 50.0 g (23.0 mmol) of Chimassorb 905 (from CIBA-GEIGY Corp.), 0.5 g of molybdenum trioxide, and 100 ml of n-octane is heated to reflux. Water is collected in a Dean-Stark trap. The remaining t-butyl hydroperoxide-octane solution is then added over 2.5 hours to the red reaction mixture. The reaction is heated at reflux for four hours after the addition, then treated with 60 g (470 mmol) of 70% t-butyl hydroperoxide and heated at reflux for another four hours to discharge the red color. The reaction mixture is cooled and solids are removed by filtration. The filtrate is stirred with 300 ml of 5% aqueous sodium sulfite, dried over magnesium sulfate, and concentrated. The residue is purified by flash chromatography (19:1 heptane:ethyl acetate) on silica gel to afford 20.2 g (27% yield) of the title compound, a yellow glass 81°–91° C.

Anal. Calcd. for $C_{188}H_{362}N_{32}O_8$: C 70.6; H 11.4; N 14.0. Found: C 68.2; H 11.0; N 14.0.

EXAMPLE 68

2,4,6-tris[N-(1-octyloxy-2,2,6,6-tetramethylpiperidin-4-yl)-n-butylamino]-1,3,5-triazine 2,4,6-Tris[N-(2,2,6,6-tetramethylpiperidin-4-yl)-n-butylamino]-1,3,5-triazine (50.0 g, 70.2 mmol) is added to a mixture of 108.4 g (842 mmol) of 70% aqueous t-butylhydroperoxide, 1.0 g of molybdenum trioxide, and 350 ml of n-octane that has been heated to 50° C. The reaction mixture is carefully brought to reflux. A Dean-Stark trap is used to remove water from the reaction. The reaction mixture is heated at reflux for 16 hours. Solids are removed by filtration, and the filtrate is concentrated to give a viscous oily residue. Purification by flash chromatography (39:1 heptane:ethyl acetate) affords 15.0 g (19% yield) of the title compound.

Anal. Calcd. for $C_{66}H_{129}N_9O_3$: C 72.3; H 11.9; N 11.5. Found: C 72.2; H 12.1; N 11.4.

EXAMPLE 69A

N,N'-bis(1-cyclohexyloxy-2,2,6,6-tetramethylpiperidin-4-yl)-N,N'-bis{2,4-bis[N-(1-cyclohexyloxy-2,2,6,6-tetramethylpiperidin-4-yl)-n-butylamino]-1,3,5-triazin-6-yl}hexamethylene diamine A solution of 19.0 g (32.1 mmol) of 1,6-bis[N,N'-1-cyclohexyloxy-2,2,6,6-tetramethylpiperidin-4-yl]aminohexane in 50 ml of toluene is added over 20 minutes to a mixture of 11.9 g (64.3 mmol) of cyanuric chloride, 100 ml of toluene, 6.8 g of sodium carbonate, and 30 ml of water that has been cooled to 0° C. The reaction temperature is maintained at 2°–5° C. during the addition. The reaction is then stirred at ambient temperature for two hours. The precipitate is filtered and washed successively with water and toluene, then dissolved in dichloromethane. The toluene solution is dried over magnesium sulfate, and evaporated to obtain a residue which is added to the dichloromethane solution. Evaporation of this solution affords 12.1 g (42% yield) of N,N'-bis(1-cyclohexyloxy-2,2,6,6-tetramethylpiperidin-4-yl)-N,N'-bis((2,4-dichloro-1,3,5-triazin-6-yl)-hexamethylene diamine.

EXAMPLE 69B

A mixture of 7.0 g (7.9 mmol) of N,N'-bis(1-cyclohexyloxy-2,2,6,6-tetramethylpiperidin-4-yl)-N,N'-bis(2,4-dichloro-1,3,5-triazin-6-yl)-hexamethylene diamine, 13.0 g (41.9 mmol) of 1-cyclohexyloxy-4-n-butylamino-2,2,6,6-tetramethylpiperidine, 2.5 g of sodium hydroxide, and 100 ml of xylene is heated at reflux under nitrogen for 30 hours. Solids are removed by filtration. The filtrate is concentrated to a residue which is partially dissolved in boiling dichloromethane. The hot solution is filtered to remove an insoluble impurity, then partially evaporated and diluted with ethanol to obtain 12.2 g (78%) of the title compound, a white powder, m.p. 254°–7° C. (dec.).

Anal. Calcd. for $C_{118}H_{216}N_{18}O_6$: C 71.5; H 11.0; N 12.7. Found: C 70.4; H 10.7; N 12.4.

EXAMPLE 70

2,4-bis[N-(1-methoxy-2,2,6,6-tetramethylpiperidin-4-yl)-n-butylamino]-6-diethylamino-1,3,5-triazine A mixture of 5.0 g (22.6 mmol) of 2,4-dichloro-6-diethylamino-1,3,5-triazine (see Example 66), 14.0 g (57.8 mmol) of 1-methoxy-4-n-butylamino-2,2,6,6-tetramethylpiperidine, 50 ml of xylene, and 1.8 g of sodium hydroxide is heated at reflux for 18 hours. Salts are removed by filtration, and the filtrate is concentrated to an oil. Purification by column chromatography (heptane) affords 9.7 g (68% yield) of the title compound, a white solid, m.p. 109°–112° C.

Anal. Calcd. for $C_{35}H_{68}N_8O_2$: C 66.4, H 10.8; N 17.7. Found: C 66.2; H 10.9; N 17.7.

EXAMPLE 71

2,4-bis[N-(1-cyclohexyloxy-2,2,6,6-tetramethylpiperidin-4-yl)-n-butylamino]-6-n-butylamino-1,3,5-triazine A mixture of 5.0 g (22.5 mmol) of 2,4-dichloro-6-n-butylamino-1,3,5-triazine, 21.1 g (67.8 mmol) of 1-cyclohexyloxy-4-n-butylamino-2,2,6,6-tetramethylpiperidine, 100 ml of xylene, and 5.4 g of 50% aqueous sodium hydroxide is heated at reflux for 16 hours. The reaction mixture is partitioned between ether and water. The ether layer is washed with 1N HCl (2×100 ml), saturated sodium bicarbonate (100 ml) and saturated sodium chloride (100 ml), then dried over magnesium sulfate and concentrated. The crude product is purified by flash chromatography (heptane) and crystallized from ethanol to afford 7.6 g (44% yield) of the title compound, a glass, m.p. 80°–86° C.

Anal. Calcd. for $C_{45}H_{84}N_8O_2$: C 70.3; H 11.0; N 14.6. Found: C 70.2; H 11.1; N 14.6.

EXAMPLE 72A

N,N'-bis{2,4-bis[N-(1-cyclohexyloxy-2,2,6,6-tetramethylpiperidin-4-yl)-n-butylamino]-1,3,5-triazin-6-yl}hexamethylene diamine A solution of 36.0 g (116 mmol) of 4-n-butylamino-1-cyclohexyloxy-2,2,6,6-tetramethylpiperidine in 100 ml of xylene is added over 20 minutes to a mixture of 10.9 g (59.2 mmol) of cyanuric chloride, 10.0 g of 50% aqueous sodium hydroxide, 10 ml of water, and 50 ml of xylene. The reaction temperature increases from 25 to 60° C. during the addition and is then maintained at 65°–70° C. for six hours. The phases are separated, and the organic phase is dried over magnesium sulfate and concentrated. The residue is purified by flash chromatography (39:1 heptane:ethyl acetate) on silica gel to afford 27.7 g (65% yield) of 2-chloro-4,6-bis-[N-(1-cyclohexyloxy-2,2,6,6-tetramethylpiperidin-4-yl)-n-butylamino]-1,3,5-triazine, a white glass, m.p. 75°–82° C.

Anal. Calcd. for $C_{41}H_{74}ClN_7O_2$: C 67.2; N 10.2; N 13.4. Found: C 68.0; H 11.0; N 13.4.

EXAMPLE 72B

A mixture of 15.0 g (20.5 mmol) of 2-chloro-4,6-bis[N-(1-cyclohexyloxy-2,2,6,6-tetramethylpiperidin-4-yl)-n-butylamino]-1,3,5-triazine, 1.19 g (10.2 mmol) of 1,6-hexanediamine, 1.0 g of sodium hydroxide, and 50 ml of toluene is heated at reflux. Water is collected in a Dean-Stark trap. Solids are removed by filtration, and the filtrate is concentrated to obtain an oil. Purification by flash chromatography (silica gel, 19:1, then 4:1 heptane:ethyl acetate) affords 4.7 g (31% yield) of the title compound, a white glass, m.p. 123°–131° C.

Anal. Calcd. for $C_{88}H_{162}N_6O_4$: C 70.1; H 10.8; N 14.9. Found: C 70.6; H 10.7; N 15.0.

EXAMPLE 73A 1,6-Bis[N,N'-bis{2,4-bis[N-1-cyclohexyloxy-2,2,6,6-tetramethylpiperidin-4-yl)-n-butylamino]-1,3,5-triazin-6-yl}-(N,N'-dimethyl)hexanediamine A solution of 15.0 g (104 mmol) of 1,6-bis(methylamino) hexane in 50 ml of toluene is added over 20 minutes to a mixture of 38.3 g (208 mmol) of cyanuric chloride, 200 ml of toluene, 22.0 g (208 mmol) of sodium carbonate, and 88 ml of water that has been cooled to 0° C. The reaction temperature is maintained at 0°–10° C. during the addition. The reaction is stirred for three hours at ambient temperature, then poured into 500 ml of water. The organic phase is dried over magnesium sulfate, concentrated, and the residue crystallized from dichloromethane-acetonitrile. The yield of 1,6-bis[N,N'-bis{2,4-dichloro-1,3,5-triazin-6-yl}](methylamino)hexane is 30.9 g (67%), m.p. 102°–106° C.

EXAMPLE 73B

A mixture of 7.0 g (15.9 mmol) of 1,6-bis{N,N'-bis(2,4-dichloro-1,3,5-triazin-6-yl),(methylamino)hexane, 20.0 g (64.4 mmol) of 1-cyclohexyloxy-4-n-butylamino-2,2,6,6-tetramethylpiperidine, 3.8 g of sodium hydroxide, and 150 ml of xylene is heated at reflux for 30 hours. Water is collected in a Dean-Stark trap and solids are removed by filtration. The filtrate is concentrated to give a viscous oil which is purified by flash chromatography (99:1 heptane:ethyl acetate). Crystallization from methanol affords 11.2 g (46% yield) of the title compound, a white solid, m.p. 137°–9° C.

Anal. Calcd. for $C_{90}H_{166}N_{16}O_4$: C 70.4; H 10.9; N 14.6. Found: C 70.2; H 10.8; N 14.3.

EXAMPLE 74

N,N'-bis{2,4-bis[N-(1-cyclohexyloxy-2,2,6,6-tetramethylpiperidin-4-yl)-n-butylamino]-1,3,5-triazin-6-yl}piperazine Piperazine (8.0 g, 92.9 mmol) is added over a 20 minute period to a mixture of 34.3 g (186 mmol) of cyanuric chloride, 19.7 g of sodium carbonate, 80 ml of water and 200 ml of toluene maintained at a temperature of 5°–10° C. The reaction mixture is stirred for 3 hours at ambient temperature. The precipitate is filtered and washed with water and toluene to obtain 26.0 g (73% yield) of N,N'-bis-(2,4-dichloro-1,3,5-triazin-6-yl)piperazine.

EXAMPLE 74B

A mixture of 2.5 g (6.54 mmol) of N,N'-bis(2,4-dichloro-1,3,5-triazin-6-yl)piperazine, 14.2 g (45.7 mmol) of 1-cyclohexyloxy-4-n-butylamino-2,2,6,6-tetramethylpiperidine, 3.6 g of 50% sodium hydroxide, and 30 ml of xylene is heated at reflux for 13 hours. Solids are removed by filtration. The residue obtained from evaporation of the filtrate is purified by flash chromatography (dichloromethane) and crystallized from dichloromethane-isopropyl alcohol to afford 6.8 g (70% yield) of the title compound, m.p. 261°–4° C. (dec.).

Anal. Calcd. for $C_{86}H_{156}N_{16}O_4$: C 69.9; H 10.6; N 15.2. Found: C 60.9; H 9.2; N 13.7.

EXAMPLE 75

N-(1-cyclohexyloxy-2,2,6,6-tetramethylpiperidin-4-yl) succinimide

A solution of 2.64 g of 1-cyclohexyloxy-4-amino-2,2,6,6-tetramethylpiperidine in 10 ml of acetone is added to a solution of 1.0 g of succinic anhydride in 25 ml of acetone. After stirring the reaction mixture at room temperature for 8 hours and removal of the solvent under reduced pressure, 3.54 g of the intermediate amide acid are obtained. A solution of the above (3.0 g), 0.1 g of sodium acetate and 3.1 ml of acetic anhydride in 10 ml of dimethylformamide is heated at 90° C. for 3 hours to effect cyclization to the desired imide. The removal of solvents under reduced pressure followed by purification utilizing $SiO_2$ flash chromatography [heptane:ethyl acetate (60:40)] and crystallization from ethyl acetate-heptane provide the desired succinimide as a white crystalline solid m.p. 133°–36° C.

Anal. Calcd. for $C_{19}H_{32}N_2O_3$: C, 67.8; H, 9.6; N, 8.3. Found: C, 67.2; H, 9.5; N, 8.1.

EXAMPLE 76

Bis-(1-norbornyloxy-2,2,6,6-tetramethylpiperidin-4-yl) sebacate

When using the general procedure of Example 31, an equivalent amount of norbornane is substituted for octadecane and the above-named compound is obtained.

EXAMPLE 77

Bis-(1-tricyclo[5.2.1.0$^{2,6}$]decyloxy-2,2,6,6-tetramethylpiperidin-4-yl) sebacate When using the general procedure of Example 31, an equivalent amount of tricyclo[5.2.1.0$^{2,6}$]decane is substituted for octadecane and the above-named compound is obtained.

EXAMPLE 78

N-(1-cyclohexyloxy-2,2,6,6-tetramethylpiperidin-4-yl) n-dodecyl succinimide

The procedure of Example 75 is repeated using 1-cyclohexyloxy-4-amino-2,2,6,6-tetramethylpiperidine and n-dodecyl succinic anhydride to afford the title compound.

EXAMPLE 79

N-(1-methoxy-2,2,6,6-tetramethylpiperidin-4-yl) n-dodecyl succinimide

The procedure of Example 75 is repeated using 1-methoxy-4-amino-2,2,6,6-tetramethylpiperidine and n-dodecyl succinic anhydride to afford the title compound.

EXAMPLE 80

N-(1-octyloxy-2,2,6,6-tetramethylpiperidin-4-yl) n-dodecyl succinimide

The procedure of Example 75 is repeated using 1-octyloxy-4-amino-2,2,6,6-tetramethylpiperidine and n-dodecyl succinic anhydride to afford the title compound.

EXAMPLE 81

N-(1-heptyloxy-2,2,6,6-tetramethylpiperidin-4-yl)-n-dodecyl succinimide

The procedure of Example 75 is repeated using 1-heptyloxy-4-amino-2,2,6,6-tetramethylpiperidine and n-dodecyl succinic anhydride to afford the title compound.

EXAMPLE 82

Tetrakis (1-cyclohexyloxy-2,2,6,6-tetramethylpiperidin-4-yl)-1,2,3,4-butanetetracarboxylate The procedure of Example 50 is repeated using 4-hydroxy-1-cyclohexyloxy-2,2,6,6-tetramethylpiperidine and tetramethyl-1,2,3,4-butanetetracarboxylate to afford the title compound.

EXAMPLE 83

Tetrakis (1-methoxy-2,2,6,6-tetramethylpiperidin-4-yl)-1,2,3,4-butanetetracarboxylate The procedure of Example 50 is repeated using 4-hydroxy-1-methoxy-2,2,6,6-tetramethylpiperidine and tetramethyl-1,2,3,4-butanetetracarboxylate to afford the title compound.

EXAMPLE 84

Tetrakis (1-octyloxy-2,2,6,6-tetramethylpiperidin-4-yl)-1,2,3,4-butanetetracarboxylate The procedure of Example 50 is repeated using 4-hydroxy-1-octyloxy-2,2,6,6-tetramethylpiperidine and tetramethyl-1,2,3,4-butanetetracarboxylate to afford the title compound.

EXAMPLE 85

Tetrakis (1-heptyloxy-2,2,6,6-tetramethylpiperidin-4-yl)-1,2,3,4-butanetetracarboxylate The procedure of Example 50 is repeated using 4-hydroxy-1-heptyloxy-2,2,6,6-tetramethylpiperidine and tetramethyl-1,2,3,4-butanetetracarboxylate to afford the title compound.

EXAMPLE 86

Mixed (1-octyloxy-2,2,6,6-tetramethyl-4-piperidyl/tridecyl)-1,2,3,4-butanetetracarboxylate The procedure of Example 84 is repeated using 4-hydroxy-1-octyloxy-2,2,6,6-tetramethylpiperidine and mixed (methyl/tridecyl)-1,2,3,4-butanetetracarboxylate to afford the title compound.

EXAMPLE 87

Mixed (1-heptyloxy-2,2,6,6-tetramethyl-4-piperidyl/tridecyl)-1,2,3,4-butanetetracarboxylate The procedure of Example 86 is repeated using an equivalent amount of 4-hydroxy-1-heptyloxy-2,2,6,6-tetramethylpiperidine instead of 4-hydroxy-1-octyloxy-2,2,6,6tetramethylpiperidine, and the above named compound is obtained.

EXAMPLE 88

Di-(1-methoxy-2,2,6,6-tetramethylpiperidin-4-yl) phthalate

A solution of 23.3 g (49 mmol) of di-(1-oxyl-2,2,6,6-tetramethylpiperidin-4-yl) phthalate, 15.0 g (103 mmol) of di-t-butyl peroxide, and 135 ml of 1,2-dichlorobenzene is heated at 145° C. in a nitrogen atmosphere for 70 minutes. The crude reaction mixture is evaporated to obtain an oil which is passed through silica gel with hexane and then 4:1 hexane:ethyl acetate as the eluent. Purification by HPLC (Waters Prep 500 A; 10:1 hexane:ethyl acetate) affords a solid which is recrystallized from heptane to give 12.5 g (50% yield) of the title compound, a white solid, m.p. 124°–26° C.

Anal. Calcd. for $C_{28}H_{44}N_2O_6$: C 66.6; H 8.8; N 5.6. Found: C 66.7; H 9.0; N 5.5.

EXAMPLE 89

(1-Methoxy-2,2,6,6-tetramethylpiperidin-4-yl)(1-octyloxy-2,2,6,6-tetramethylpiperidin-4-yl)sebacate A solution of 40.0 g (78 mmol) of di-(1-oxyl-2,2,6,6-tetramethylpiperidin-4-yl) sebacate, 15.1 g (103 mmol) of di-t-butyl peroxide, and 85 ml of chlorobenzene is heated in a Fischer-Porter bottle (nitrogen atmosphere) for 3 hours at 155°–160° C. The crude reaction mixture is passed through silica gel with 10:1 heptane:ethyl acetate as the eluent to obtain 22 g of red oil. Further purification (Waters Prep 500 A HPLC; 10:1 hexane:ethyl acetate) affords 6.4 g of (1-methoxy-2,2,6,6-tetramethylpiperidin-4-yl)(1-oxyl-2,2,6,6-tetramethylpiperidin-4-yl)sebacate.

A mixture of 6.4 g (12.2 mmol) of (1-methoxy-2,2,6,6-tetramethylpiperidin-4-yl)(1-oxyl-2,2,6,6-tetramethylpiperidin-4-yl)sebacate, 0.1 g of molybdenum trioxide, and 25 ml of n-octane is heated to 115° C. To this mixture is added dropwise 4.3 g (33 mmol) of 70% aqueous t-butyl hydroperoxide over 20 minutes. The reaction mixture is maintained at reflux during the addition and water is collected in a Dean-Stark trap. The red reaction mixture is heated at reflux for 5.25 hours after the hydroperoxide addition is complete in order to discharge the color. Solids are removed by filtration, and the filtrate is evaporated to obtain a light yellow oil which is purified by chromatography (Waters Prep. 500 A HPLC, 20:1 hexane:ethyl acetate) to afford 4.4 g of the title compound, a colorless oil. Mass spec. molecular ion=638.

EXAMPLE 90

Bis(1-methoxy-2,2,6,6-tetramethylpiperidin-4-yl)hydrazinedicarboxylate

The reaction of 1-methoxy-4-hydroxy-2,2,6,6-tetramethylpiperidine and 1,2-dicarbethoxyhydrazine in the presence of lithium amide in toluene yields the title compound as white crystals, m.p. 141°–144° C.

Anal. Calcd. for $C_{22}H_{42}N_4O_6$: C, 57.6; H, 9.2; N, 12.2. Found: C, 58.0; H, 9.5; N, 12.1.

Summarizing, this invention is seen to provide a series of new $OR_1$-substituted N-hydroxy hindered amine stabilizers. Variations may be made in proportions, procedures and materials without departing from the scope of the invention as defined by the following claims.

What is claimed is:

1. A compound corresponding to the formulae

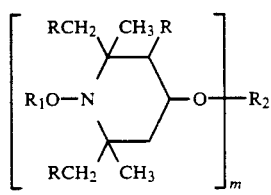

(A)

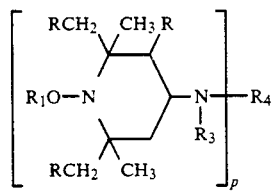

(B)

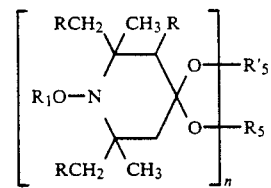

(C)

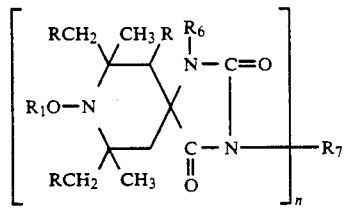

(D)

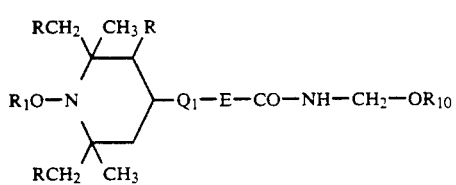

(E)

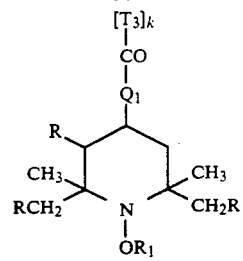

(F)

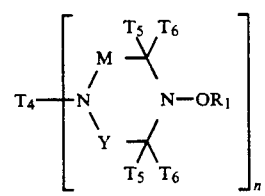

(G)

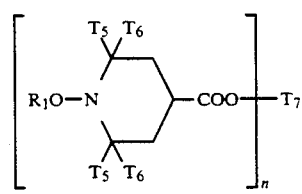

(H)

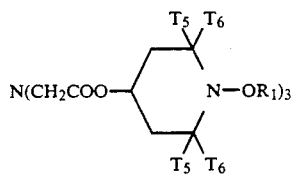

(I)

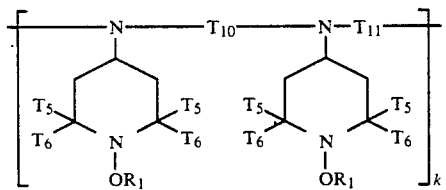

(J)

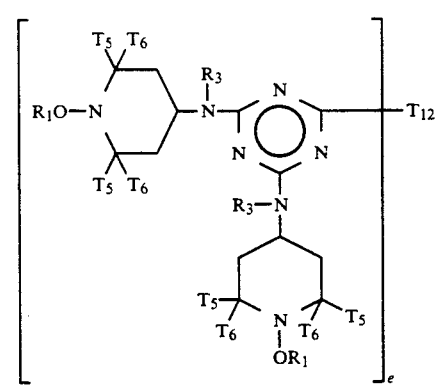

(K)

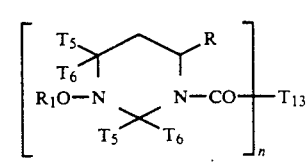

(L)

-continued

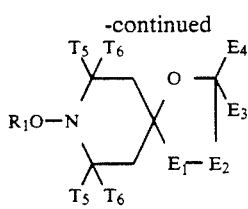 (M)

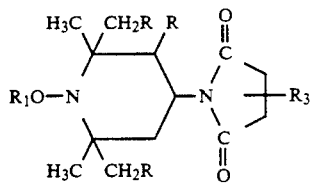 (N)

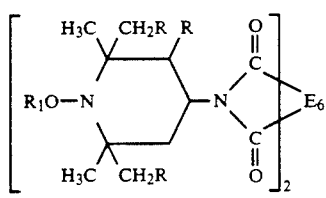 (O)

wherein
R is hydrogen or methyl,
$R_1$ is independently $C_1$-$C_{18}$ alkyl, $C_2$-$C_{18}$ alkenyl, $C_2$-$C_{18}$ alkynyl, $C_5$-$C_8$ cycloalkenyl, $C_5$-$C_{12}$ cycloalkyl, $C_6$-$C_{10}$ bicycloalkyl, $C_6$-$C_{10}$ aryl, $C_7$-$C_9$ aralkyl, or $C_7$-$C_9$ aralkyl substituted by alkyl or $C_6$-$C_{10}$ aryl;
m is 2-4,
when m is 2,
$R_2$ is $C_1$-$C_{12}$ alkylene, $C_4$-$C_{12}$ alkenylene, xylylene, a divalent acyl radical of an aliphatic, cycloaliphatic, araliphatic or aromatic carboxylic acid, or of a dicarbamic acid,

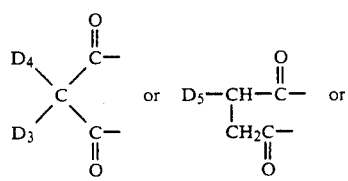

wherein $D_3$ and $D_4$ are independently hydrogen, an alkyl radical containing up to 8 carbon atoms, an $C_6$-$C_{10}$ aryl or an $C_7$-$C_9$ aralkyl or 3,5-di-tert-butyl-4-hydroxybenzyl radical, $D_5$ is hydrogen, or an alkyl or alkenyl radical containing up to 18 carbon atoms, and d is 0-20;
when m is 4, $R_2$ is a trivalent acyl radical of an aliphatic, unsaturated aliphatic, cycloaliphatic, or aromatic tricarboxylic acid;
when m is 4, $R_2$ is a tetravalent acyl radical of a saturated or unsaturated aliphatic or aromatic tetracarboxylic acid,
p is 1, 2 or 3,
$R_3$ is hydrogen, $C_1$-$C_{12}$ alkyl, $C_5C_7$ cycloalkyl, $C_7$-$C_8$ aralkyl, $C_2$-$C_{18}$ alkanoyl, $C_3$-$C_5$ alkenoyl or benzoyl;
when p is 1, $R_4$ is hydrogen, $C_1$-$C_{18}$ alkyl $C_5C_7$ cycloalkyl, $C_2$-$C_8$ alkenyl unsubstituted or substituted by a cyano, carbonyl or carbamide group, $C_6$-$C_{10}$ aryl, $C_7$-$C_9$ aralkyl, glycidyl, a group of the formula —CH$_2$—CH(OH)—Z or of the formula —CO—Z— or —CONH—Z wherein Z is hydrogen, methyl or phenyl; or a group of the formulae

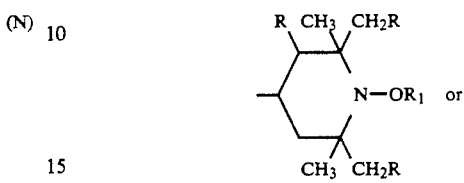

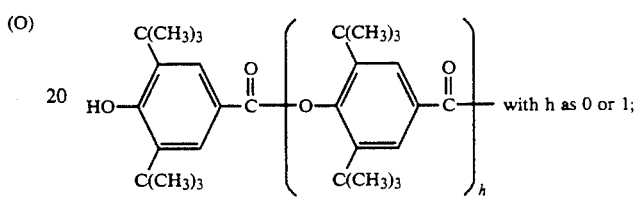 with h as 0 or 1;

or $R_3$ and $R_4$ together when p is 1 can be alkylene of 4 to 6 carbon atoms or 2-oxapolyalkylene or the cyclic acyl radical of an aliphatic or aromatic 1,2- or 1,3-dicarboxylic acid,
when p is 2,
$R_4$ is a direct bond or is $C_1$-$C_{12}$ alkylene, $C_6$-$C_{12}$ arylene, xylylene, a —CH$_2$CH(OH)—CH$_2$ group, or a group —CH$_2$—CH(OH)—CH$_2$—O—X—O—CH$_2$ —CH(OH)—CH$_2$— wherein X is $C_2$-$C_{10}$ alkylene, $C_6$-$C_{15}$ arylene or $C_6$-$C_{12}$ cycloalkylene; or, provided that $R_3$ is not alkanoyl, alkenoyl or benzoyl, $R_4$ can also be a divalent acyl radical of an aliphatic, cycloaliphatic or aromatic dicarboxylic acid or of a dicarbamic acid, or can be the group —CO—; or
$R_4$ is

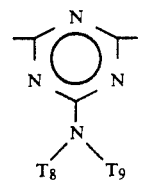

where $T_8$ and $T_9$ are independently hydrogen, alkyl of 1 to 18 carbon atoms, or $T_8$ and $T_9$ together are alkylene of 4 to 6 carbon atoms or 3-oxapentamethylene,
when p is 3,
$R_4$ is 2,4,6-triazinyl,
n is 1 or 2,
when n is 1,
$R_5$ and $R'_5$ are independently $C_1$-$C_{12}$ alkyl, $C_2$-$C_{12}$ alkenyl, $C_7$-$C_{12}$ aralkyl, or $R_5$ is also hydrogen, or $R_5$ and $R'_5$ together are $C_2$-$C_8$ alkylene or $C_2$-$C_8$ hydroxyalkylene or $C_4$-$C_{22}$ acyloxyalkylene;
when n is 2,
$R_5$ $R'_5$ together are (—CH$_2$)$_2$C(CH$_2$—)$_2$;
$R_6$ is hydrogen, $C_1$-$C_{12}$ alkyl, allyl, benzyl, glycidyl or $C_2$-$C_6$ alkoxyalkyl;
when n is 1, $R_7$ is hydrogen, $C_1$-$C_{12}$ alkyl, $C_3$-$C_5$ alkenyl, $C_7$-$C_9$ aralkyl, $C_5$-$C_7$ cycloalkyl, $C_2$-$C_4$ hydroxyalkyl, $C_2$-$C_6$ alkoxyalkyl, $C_6$-$C_{10}$ aryl, glycidyl, a group of the formula —$(CH_2)_t$—COO—Q or of the formula —$(CH_2)_t$—O—CO—Q wherein t is 1 or 2, and Q is $C_1$-$C_4$ alkyl or phenyl; or when n is 2, $R_7$ is $C_2$-$C_{12}$ alkylene, $C_6$-$C_{12}$ arylene, a group —$CH_2CH(OH)$—$CH_2$—O—X—O—$CH_2$—CH(OH)—$CH_2$— wherein X is $C_2$-$C_{10}$ alkylene, $C_6$-$C_{15}$ arylene or $C_6$-$C_{12}$ cycloalkylene, or a group —$CH_2CH(OZ')CH_2$—$(OCH_2$—CH(OZ')CH_2)_2$— wherein Z' is hydrogen, $C_1$-$C_{18}$ alkyl, allyl, benzyl, $C_2$-$C_{12}$ alkanoyl or benzoyl;

$Q_1$ is —$N(R_8)$— or —O—;

E is $C_1$-$C_3$ alkylene, the group —$CH_2$—$CH(R_9)$—O— wherein $R_9$ is hydrogen, methyl or phenyl, the group —$(CH_2)_3$—NH— or a direct bond;

$R_{10}$ is hydrogen or $C_1$-$C_{18}$ alkyl, $R_8$ is hydrogen, $C_1$-$C_{18}$ alkyl, $C_5$-$C_7$ cycloalkyl, $C_7$-$C_{12}$ aralkyl, cyanoethyl, $C_6$-$C_{10}$ aryl, the group —$CH_2$—$CH(R_9)$—OH wherein $R_9$ has the meaning defined above; a group of the formula

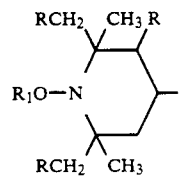

or a group of the formula

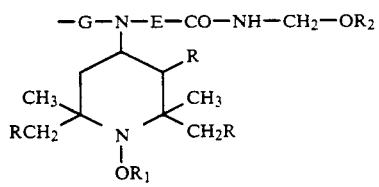

wherein G is $C_2$-$C_6$ alkylene or $C_6$-$C_{12}$ arylene; or $R_8$ is a group —E—CO—NH—$CH_2$—$OR_{10}$;

$T_3$ is ethylene or 1,2-propylene, or is the repeating structural unit derived from an alpha-olefin copolymer with an alkyl acrylate or methacrylate;

k is 2 to 100;

$T_4$ has the same meaning as $R_4$ when p is 1 or 2, $T_5$ is methyl, $T_6$ is methyl or ethyl, or $T_5$ and $T_6$ together are tetramethylene or pentamethylene, M and Y are independently methylene or carbonyl;

$T_7$ is the same as $R_7$, $T_{10}$ and $T_{11}$ are independently alkylene of 2 to 12 carbon atoms, or $T_{11}$ is

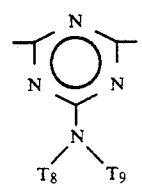

$T_{12}$ is piperazinyl, —$NR_{11}$—$(CH_2)_d$—$NR_{11}$— or

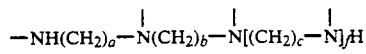

where $R_{11}$ is the same as $R_3$ and is also

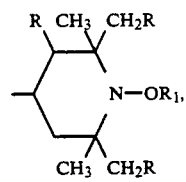

a, b and c are independently 2 or 3, and f is 0 or 1, e is 2, 3 or 4;

$T_{13}$ is the same as $R_2$ with the proviso that $T_{13}$ cannot be hydrogen when n is 1;

$E_1$ and $E_2$, being different, each are —CO— or —N($E_5$) where $E_5$ is hydrogen, $C_1$-$C_{12}$ alkyl or alkoxycarbonylalkyl of 4 to 22 carbon atoms;

$E_3$ is hydrogen, alkyl of 1 to 30 carbon atoms, phenyl, naphthyl, said phenyl or said naphthyl substituted by chlorine or by alkyl of 1 to 4 carbon atoms, or phenylalkyl of 7 to 12 carbon atoms, or said phenylalkyl substituted by alkyl of 1 to 4 carbon atoms, $E_4$ is hydrogen, alkyl of 1 to 30 carbon atoms, phenyl, naphthyl or phenylalkyl of 7 to 12 carbon atoms, or $E_3$ and $E_4$ together are polymethylene of 4 to 17 carbon atoms, or said polymethylene substituted by up to four alkyl groups of 1 to 4 carbon atoms, and $E_6$ is an aliphatic or aromatic tetravalent radical, and with the proviso that in formula B when $R_1$ is alkyl, $R_3$ is not hydrogen.

2. The compounds of formulae (A), (B), (J) and (K) according to claim 1.

3. The compound of formula A according to claim 2, wherein m is 2 and $R_2$ is an acyl radical of an aliphatic dicarboxylic acid having 2-18 C atoms.

4. The compound of claim 3, wherein said acid is succinic, sebacic, phthalic, isophthalic or terephthalic acid.

5. The compound of claim 3, wherein $R_1$ is $C_1$-$C_{12}$ alkyl or cyclohexyl.

6. The compound of claim 1 selected from the group consisting of di-(1-methoxy-2,2,6,6-tetramethylpiperidin-4-yl) isophthalate, di-(1-methoxy-2,2,6,6-tetramethylpiperidin-4-yl) sebacate, alpha,alpha'-(di-1-ethoxy-2,2,6,6-tetramethylpiperidin-4-yl oxy)-p-xylene, di-(1-cyclohexyloxy-2,2,6,6-tetramethylpiperidin-4-yl) sebacate, di-(1-cyclohexyloxy-2,2,6,6-tetramethylpiperidin-4-yl) isophthalate, alpha,alpha'-(di-1-benzyloxy-2,2,6,6-tetramethylpiperidin-4-yloxy)-p-xylene, di-(1-benzyloxy-2,2,6,6-tetramethylpiperidin-4-yl) sebacate, di-(1-benzyloxy-2,2,6,6-tetramethylpiperidin-4-yl) phthalate, di-(1-benzyloxy-2,2,6,6-tetramethylpiperidin-4-yl) isophthalate, di-(1-benzyloxy-2,2,6,6-tetramethylpiperidin-4-yl) diethylmalonate, di-[1-(alpha-methylbenzyloxy)-2,2,6,6-tetramethylpiperidin-4-yl] phthalate,
di-[1-(alpha-methylbenzyloxy)-2,2,6,6-tetramethylpiperidine-4-yl] sebacate,
di-(1-heptyloxy-2,2,6,6-tetramethylpiperidin-4-yl) sebacate,
di-(1-alpha-methylbenzyloxy-2,2,6,6-tetramethylpiperidin-4-yl) terephthalate,
di-(1-alpha-methylbenzyloxy-2,2,6,6-tetramethylpiperidin-4-yl) isophthalate,
di-(1-ethoxy-2,2,6,6-tetramethylpiperidin-4-yl) sebacate,
di-(1-cumyloxy-2,2,6,6-tetramethylpiperidin-4-yl) sebacate,
8-alpha-methylbenzyloxy-7,7,9,9-tetramethyl-8-aza-1,4-dioxaspiro[4.5]decane,
3,15-di-alpha-methylbenzyloxy-2,2,4,4,14,14,16,16-octamethyl-7,11,18,21-tetraoxa-3,15-diazatrispiro-5.2.2.5.2.2.]heneicosane,
3,15-dicyclohexyloxy-2,2,4,4,14,14,16,16-octamethyl-7,11,18,21-tetraoxa-3,15-diazatrispiro[5.2.2.5.2.2.-]heneicosane,
di-(1-methoxy-2,2,6,6-tetramethylpiperidin-4-yl) n-butylmalonate,
di-(1-methoxy-2,2,6,6-tetramethylpiperidin-4-yl) (3,5-di-t-butyl-4-hydroxybenzyl)-n-butylmalonate,
di-(1-cyclohexyloxy-2,2,6,6-tetramethylpiperidin-4-yl) n-butylmalonate,
di-(1-cyclohexyloxy-2,2,6,6-tetramethylpiperidin-4-yl) (3,5-di-t-butyl-4-hydroxybenzyl)-n-butylmalonate,
poly-{[6-(1,1,3,3-tetramethylbutyl)-imino]-1,3,5-triazine-2,4-diyl] [2-(1-cyclohexyloxy-2,2,6,6-tetramethylpiperidyl)-imino]-hexamethylene-[4-(1-cyclohexyloxy-2,2,6,6-tetramethylpiperidyl)-imino]},
di-(1-cyclohexyloxy-2,2,6,6-tetramethylpiperidin-4-yl) succinate,
di-(1-alpha-methylbenzyloxy-2,2,6,6-tetramethylpiperidin-4-yl) succinate,
di-(1-nonyloxy-2,2,6,6-tetramethylpiperidin-4-yl) sebacate,
di-(1-octadecyloxy-2,2,6,6-tetramethylpiperidin-4-yl) sebacate,
di-(1-cyclohexyloxy-2,2,6,6-tetramethylpiperidin-4-yl) phthalate,
(1-cyclohexyloxy-2,2,6,6-tetramethylpiperidin-4-yl) (1-methoxy-2,2,6,6-tetramethylpiperidin-4-yl) phthalate,
1-cyclohexyloxy-4-(n-dodecylamino)-2,2,6,6-tetramethylpiperidine,
1-alpha-methylbenzyloxy-4-(n-dodecylamino)-2,2,6,6-tetramethylpiperidine,
1-alpha-methylbenzyloxy-4-(n-butylamino)-2,2,6,6-tetramethylpiperidine,
N,N'-di-(1-cyclohexyloxy-2,2,6,6-tetramethylpiperidin-4-yl)-1,6-hexanediamine,
1-cyclohexyloxy-4-(n-butylamino)-2,2,6,6-tetramethylpiperidine,
di-(1-nonyloxy-2,2,6,6-tetramethylpiperidin-4-yl) succinate,
di-(1-decyloxy-2,2,6,6-tetramethylpiperidin-4-yl) sebacate,
di-(1-dodecyloxy-2,2,6,6-tetramethylpiperidin-4-yl) sebacate,
di-[1-(1-methylcyclohexyloxy)-2,2,6,6-tetramethylpiperidin-4-yl] sebacate,
di-[1-(2-cyclohexen-1-yloxy)-2,2,6,6-tetramethylpiperidin-4-yl] sebacate,
di-(1-t-butoxy-2,2,6,6-tetramethylpiperidin-4-yl) sebacate,
di-(1-methoxy-2,2,6,6-tetramethylpiperidin-4-yl)succinate,
4-acetamido-1-cyclohexyloxy-2,2,6,6-tetramethylpiperidine,
4-amino-1-cyclohexyloxy-2,2,6,6-tetramethylpiperidine,
N,N'-bis[1-cyclohexyloxy-2,2,6,6-tetramethylpiperidin-4-yl]succinamide,
bis(1-methoxy-2,2,6,6-tetramethylpiperidin-4-yl)succinate,
bis(1-octyloxy-2,2,6,6-tetramethylpiperidin-4-yl)succinate,
bis(1-methoxy-2,2,6,6-tetramethylpiperidin-4-yl)terephthalate,
bis[N-(1-cyclohexyloxy-2,2,6,6-tetramethylpiperidin-4-yl)-N-n-butyl]sebacamide,
bis[N-(1-octyloxy-2,2,6,6-tetramethylpiperidin-4-yl]-N-n-butyl]sebacamide,
1,6-bis[N,N'-di-(1-cyclohexyloxy-2,2,6,6-tetramethylpiperidin-4-yl)-acetylamino]hexane,
bis(1-cyclooctyloxy-2,2,6,6-tetramethylpiperidin-4-yl)sebacate,
bis(1-octyloxy-2,2,6,6-tetramethylpiperidin-4-yl)sebacate,
bis(1-heptyloxy-2,2,6,6-tetramethylpiperidin-4-yl)succinate,
bis(1-decahydronaphthalenyloxy-2,2,6,6-tetramethylpiperidin-4-yl)sebacate,
bis(1-cyclododecyloxy-2,2,6,6-tetramethylpiperidin-4-yl)sebacate,
N,N',N'',N'''-tetrakis{2,4-bis[N-(1-cyclohexyloxy-2,2,6,6-tetramethylpiperidin-4-yl)-n-butylamino]-1,3,5-triazin-6-yl}-3,3'-ethylenediiminodipropylamine,
2,4,6-tris[N-(1-cyclohexyloxy-2,2,6,6-tetramethylpiperidin-4-yl)-n-butylamino]-1,3,5-triazine,
2,4-bis[N-(1-cyclohexyloxy-2,2,6,6-tetramethylpiperidin-4-yl)-n-butylamino]-6-t-octylamino-1,3,5-triazine,
2,4-bis[N-(1-cyclohexyloxy-2,2,6,6-tetramethylpiperidin-4-yl)-n-butylamino]-6-morpholino-1,3,5-triazine,
2,4-bis[N-(1-cyclohexyloxy-2,2,6,6-tetramethylpiperidin-4-yl)-n-butylamino]-6-diethylamino-1,3,5-triazine,
N,N',N'',N'''-tetrakis{2,4-bis[N-(1-octyloxy-2,2,6,6-tetramethylpiperidin-4-yl)-n-butylamino]-1,3,5-triazin-6-yl}-3,3'-ethylenediiminodipropylamine,
2,4,6-tris[N-(1-octyloxy-2,2,6,6-tetramethylpiperidin-4-yl) n-butylamino]-1,3,5-triazine,
N,N'-bis(1-cyclohexyloxy-2,2,6,6-tetramethylpiperidin-4-yl) N,N'-bis{2,4-bis[N-(1-cyclohexyloxy-2,2,6,6-tetramethylpiperidin-4-yl)-n-butylamino]-1,3,5-triazin-6-yl}hexamethylene diamine,
2,4-bis[N-(1-methoxy-2,2,6,6-tetramethylpiperidin-4-yl)-n-butylamino]-6-diethylamino-1,3,5-triazine,
2,4-bis[N-(1-cyclohexyloxy-2,2,6,6-tetramethylpiperidin-4-yl)-n-butylamino]-6-n-butylamino-1,3,5-triazine,
N,N'-bis{2,4-bis[N-(1-cyclohexyloxy-2,2,6,6-tetramethylpiperidin-4-yl)-n-butylamino]-1,3,5-triazin-6-yl}hexamethylene diamine,
1,6-bis[N,N'-bis{2,4-bis[N-1-cyclohexyloxy-2,2,6,6-tetramethylpiperidin-4-yl)-n-butylamino]-1,3,5-triazin-6-yl}](N,N'-dimethyl)hexanediamine,
N,N'-bis{2,4-bis[N-(1-cyclohexyloxy-2,2,6,6-tetramethylpiperidin-4-yl)-n-butylamino]-1,3,5-triazin-6-yl}piperazine,
N-(1-cyclohexyloxy-2,2,6,6-tetramethylpiperidin-4-yl) succinimide, bis-(1-norbornyloxy-2,2,6,6-tetramethylpiperidin-4-yl) sebacate, bis-(1-tricyclo[5.2.1.0$^{2,6}$]decyloxy-2,2,6,6-tetramethylpiperidin-4-yl) sebacate, N-(1-cyclohexyloxy-2,2,6,6-tetramethylpiperidin-4-yl) n-dodecyl succinimide, N-(1-methoxy-2,2,6,6-tetramethylpiperidin-4-yl) n-dodecyl succinimide, N-(1-octyloxy-2,2,6,6-tetramethylpiperidin-4-yl) n-dodecyl succinimide, N-(1-heptyloxy-2,2,6,6-tetramethylpiperidin-4-yl)-n-dodecyl succinimide, tetrakis (1-cyclohexyloxy-2,2,6,6-tetramethylpiperidin-4-yl)-1,2,3,4-butanetetracarboxylate, tetrakis (1-methoxy-2,2,6,6-tetramethylpiperidin-4-yl)-1,2,3,4-butanetetracarboxylate, tetrakis (1-octyloxy-2,2,6,6-tetramethylpiperidin-4-yl)-1,2,3,4-butanetetracarboxylate, tetrakis (1-heptyloxy-2,2,6,6-tetramethylpiperidin-4-yl)-1,2,3,4-butanetetracarboxylate, di-(1-methoxy-2,2,6,6-tetramethylpiperidin-4-yl) phthalate, (1-methoxy-2,2,6,6-tetramethylpiperidin-4-yl)(1-octyloxy-2,2,6,6-tetramethylpiperidin-4-yl)sebacate, bis(1-methoxy-2,2,6,6-tetramethylpiperidin-4-yl)hydrazinedicarboxylate, bis[N-(1-methoxy-2,2,6,6-tetramethylpiperidin-4-yl)-N-n-butyl]oxamide, and bis[N-(1-cyclohexyloxy-2,2,6,6-tetramethylpiperidin-4-yl)-N-n-butyl]oxamide.

7. Di-(1-cyclohexyloxy-2,2,6,6-tetramethylpiperidin-4-yl) sebacate according to claim 1.

8. Di-(1-cyclohexyloxy-2,2,6,6-tetramethylpiperidin-4-yl) isophthalate according to claim 1.

9. Di-(1-heptyloxy-2,2,6,6-tetramethylpiperidin-4-yl) sebacate according to claim 1.

10. 3,15-Dicyclohexyloxy-2,2,4,4,14,14,16,16-octamethyl-7,11,18,21-tetraoxa-3,15-diazatrispiro[5.2.2.5.2.2.]heneicosane according to claim 1.

11. Di-(1-cyclohexyloxy-2,2,6,6-tetramethylpiperidin-4-yl) succinate according to claim 1.

12. Di-(1-octyloxy-2,2,6,6-tetramethylpiperidin-4-yl) sebacate according to claim 1.

13. (1-Methoxy-2,2,6,6-tetramethylpiperidin-4-yl) (1-octyloxy-2,2,6,6-tetramethylpiperidin-4-yl)sebacate according to claim 1.

14. Di-(1-methoxy-2,2,6,6-tetramethylpiperidin-4-yl) succinate according to claim 1.

15. Di-(1-octyloxy-2,2,6,6-tetramethylpiperidin-4-yl) succinate according to claim 1.

16. Di-(1-heptyloxy-2,2,6,6-tetramethylpiperidin-4yl) succinate according to claim 1.

17. Di-(1-methoxy-2,2,6,6-tetramethylpiperidin-4-yl) isophthalate according to claim 1.

18. Di-(1-methoxy-2,2,6,6-tetramethylpiperidin-4-yl) phthalate according to claim 1.

19. Di-(1-cyclohexyloxy-2,2,6,6-tetramethylpiperidin-4-yl) phthalate according to claim 1.

20. Di-(1-methoxy-2,2,6,6-tetramethylpiperidin-4-yl) terephthalate according to claim 1.

21. Di-(1-cyclohexyloxy-2,2,6,6-tetramethylpiperidin-4-yl) terephthalate according to claim 1.

22. Poly-{[6-(1,1,3,3-tetramethylbutyl)-imino]-1,3,5-triazine-2,4-diyl] [2-(1-cyclohexyloxy-2,2,6;6-tetramethylpiperidyl)-imino]-hexamethylene-[4-(1-cyclohexyloxy-2,2,6,6-tetramethylpiperidyl)-imino]} according to claim 1.

23. Poly-{[6-(1,1,3,3-tetramethylbutyl)-imino]-1,3,5-triazine-2,4-diyl] [2-(1-methoxy-2,2,6,6-tetramethylpiperidyl)imino]-hexamethylene-[4-(1-methoxy-2,2,6,6-tetramethylpiperidyl)-imino]} according to claim 1.

24. N,N',N'',N'''-tetrakis{2,4-bis[N-(1-cyclohexyloxy-2,2,6,6-tetramethylpiperidin-4-yl)-n-butylamino]-1,3,5-triazin-6-yl}-3,3'-ethylenediiminodipropylamine according to claim 1.

25. N,N',N'',N'''-tetrakis{2,4-bis[N-(1-methoxy-2,2,6,6-tetramethylpiperidin-4-yl)-n-butylamino]-1,3,5-triazin-6-yl}-3,3'-ethylenediiminodipropylamine according to claim 1.

26. 2,4,6-tris[N-(1-cyclohexyloxy-2,2,6,6-tetramethylpiperidin-4-yl)-n-butylamino]-1,3,5-triazine according to claim 1.

27. N-(1-cyclohexyloxy-2,2,6,6-tetramethylpiperidin-4-yl) succinimide according to claim 1.

28. N-(1-cyclohexyloxy-2,2,6,6-tetramethylpiperidin-4-yl) n-dodecyl succinimide according to claim 1.

29. N-(1-methoxy-2,2,6,6-tetramethylpiperidin-4-yl) n-dodecyl succinimide according to claim 1.

30. N-(1-octyloxy-2,2,6,6-tetramethylpiperidin-4-yl) n-dodecyl succinimide according to claim 1.

31. N-(1-heptyloxy-2,2,6,6-tetramethylpiperidin-4-yl)-n-dodecyl succinimide according to claim 1.

32. Tetrakis (1-cyclohexyloxy-2,2,6,6-tetramethylpiperidin-4-yl)-1,2,3,4-butanetetracarboxylate according to claim 1.

33. Tetrakis (1-methoxy-2,2,6,6-tetramethylpiperidin-4-yl)-1,2,3,4-butanetetracarboxylate according to claim 1.

34. Tetrakis (1-octyloxy-2,2,6,6-tetramethylpiperidin-4-yl)-1,2,3,4-butanetetracarboxylate according to claim 1.

35. Tetrakis (1-heptyloxy-2,2,6,6-tetramethylpiperidin-4-yl)-1,2,3,4-butanetetracarboxylate according to claim 1.

36. Di-(1-methoxy-2,2,6,6-tetramethylpiperidin-4-yl) sebacate according to claim 1.

* * * * *